United States Patent
Banko

(10) Patent No.: US 11,690,757 B2
(45) Date of Patent: Jul. 4, 2023

(54) SURGICAL HAND PIECE WITH POST-OCCLUSION SURGE ELIMINATION

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 331 days.

(21) Appl. No.: 16/240,513

(22) Filed: Jan. 4, 2019

(65) Prior Publication Data

US 2019/0209374 A1 Jul. 11, 2019

Related U.S. Application Data

(63) Continuation-in-part of application No. 15/941,366, filed on Mar. 30, 2018, now Pat. No. 11,207,212.

(51) Int. Cl.
*A61F 9/007* (2006.01)

(52) U.S. Cl.
CPC .... *A61F 9/00745* (2013.01); *A61B 2217/005* (2013.01); *A61B 2217/007* (2013.01)

(58) Field of Classification Search
CPC ........ A61B 2217/005; A61B 2217/007; A61B 2017/320069–320098; A61B 2018/00595; A61B 2018/00577; A61B 2018/0063; A61B 2018/00601; A61B 2018/00589; A61B 17/320068; A61F 9/00745
USPC .................................................. 606/169, 179
See application file for complete search history.

(56) References Cited

U.S. PATENT DOCUMENTS

| | | | |
|---|---|---|---|
| 5,062,827 A * | 11/1991 | Wiksell | B06B 3/00 604/22 |
| 5,254,082 A * | 10/1993 | Takase | A61B 17/320068 604/22 |
| 5,359,996 A | 11/1994 | Hood | |
| 5,693,062 A | 12/1997 | Stegmann et al. | |
| 5,695,461 A | 12/1997 | Shaible | |
| 5,709,698 A | 1/1998 | Adams | |
| 6,592,541 B1 * | 7/2003 | Kurwa | A61F 9/00745 604/521 |
| 8,951,272 B2 | 2/2015 | Robertson | |
| 9,320,648 B2 * | 4/2016 | DeTurk | A61F 9/00745 |

(Continued)

FOREIGN PATENT DOCUMENTS

DE   10 2015 207 150 A1   11/2016
WO   WO 2008/118709 A1   10/2008

OTHER PUBLICATIONS

U.S. Appl. No. 15/783,806, filed Oct. 13, 2017, Banko.

(Continued)

*Primary Examiner* — Sarah A Simpson
(74) *Attorney, Agent, or Firm* — Leason Ellis LLP

(57) ABSTRACT

A work tip for a surgical hand piece has a solid blade connected to a source of ultrasonic energy in the hand piece. The knife has grooves in its surfaces. The work tip further including an irrigation and aspiration tubes extending along opposite surfaces of the blade and being at least partially within the grooves. The blade has a collar adjacent its distal end and at least the aspiration tube extends ends at a distance from the collar. The edges of the collar are made sharp enough to emulsify cataract tissue when vibrated at ultrasonic frequencies so that occlusion of the aspiration tube is prevented.

3 Claims, 25 Drawing Sheets

(56) References Cited

U.S. PATENT DOCUMENTS

| | | | |
|---|---|---|---|
| 2002/0111608 A1 | 8/2002 | Baerveldt et al. | |
| 2003/0229344 A1 | 12/2003 | Dycus et al. | |
| 2005/0049546 A1 | 3/2005 | Messerly et al. | |
| 2011/0196399 A1 | 8/2011 | Robertson et al. | |
| 2014/0163595 A1 | 6/2014 | Witt et al. | |
| 2014/0276369 A1 | 9/2014 | Banko | |
| 2015/0126994 A1 | 5/2015 | Matsui et al. | |
| 2017/0340344 A1* | 11/2017 | Boudreaux | A61B 17/320068 |

OTHER PUBLICATIONS

New Phaco Tip Geometry Balances Power, Suction, *Ophthalmology Times*, Jul. 15, 1992, vol. 17, No. 14, 3 pages.
Funnel-shaped tip Controls Ultrasound Energy during Phaco, *Ocular Surgery News*, Jul. 1, 1992, vol. 10, No. 13.
International Preliminary Report on Patentability PCT Application No. PCT/US2019/024910, datedOct. 6, 2020.
International Search Report and Written Opinion in corresponding PCT Application No. PCT/US2019/024910, dated Jun. 24, 2019.
International Search Report and Written Opinion in corresponding PCT Application No. PCT/US 2020/012388, dated Apr. 20, 2020.
Non-Final Office Action in corresponding U.S. Appl. No. 15/941,366, dated Feb. 18, 2020.
International Search Report and Written Opinion in corresponding PCT Application No. PCT/US2020/054389, dated Feb. 4, 2021.
International Preliminary Report on Patentability in corresponding PCT Application No. PCT/US 2020/012388, dated Jun. 16, 2021.

* cited by examiner

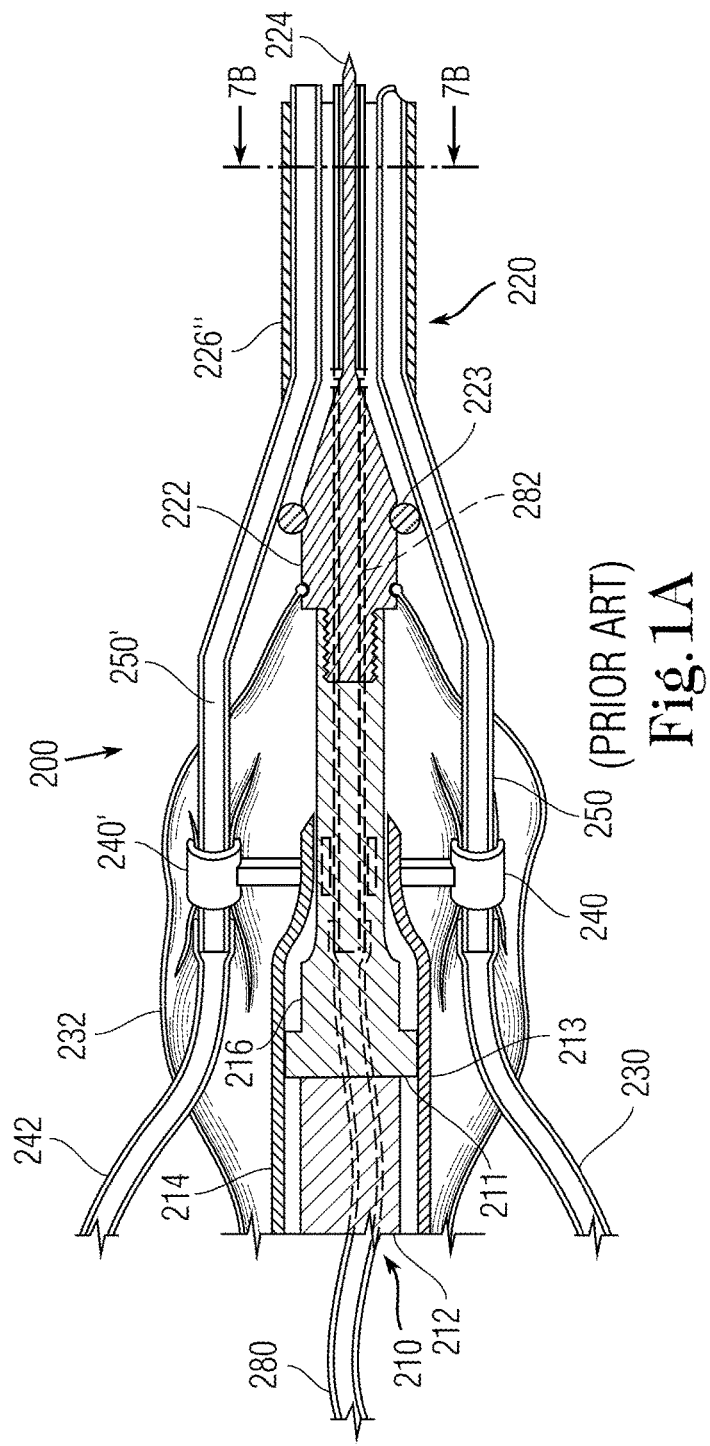
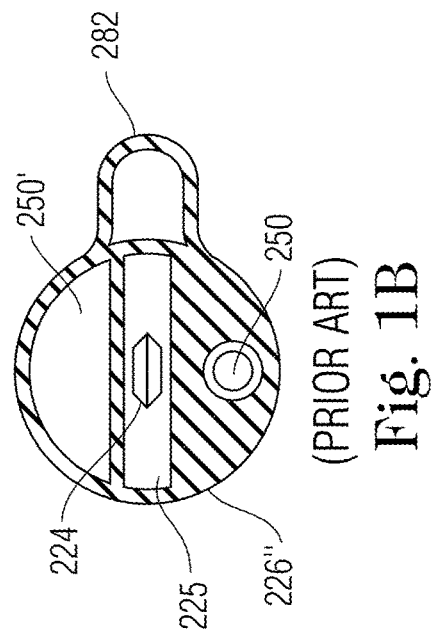
Fig. 1A (PRIOR ART)
Fig. 1B (PRIOR ART)

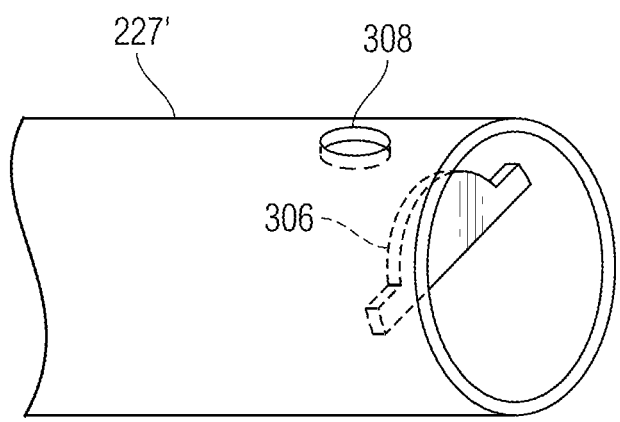
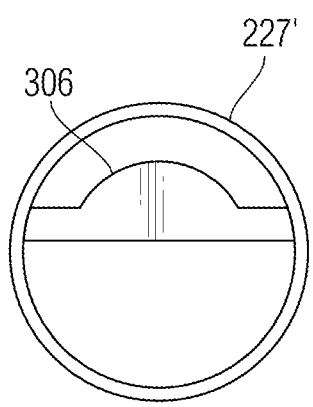
Fig. 4A    Fig. 4B
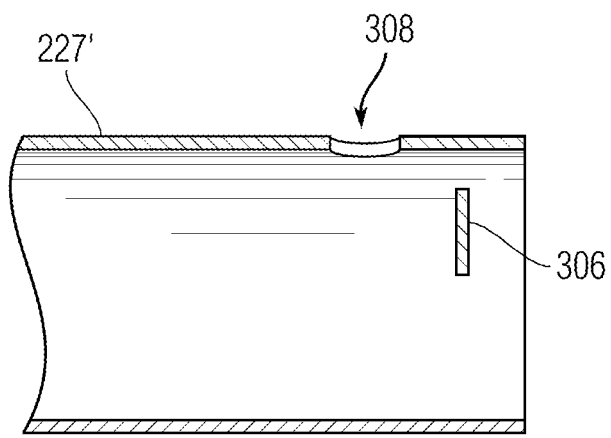
Fig. 4C

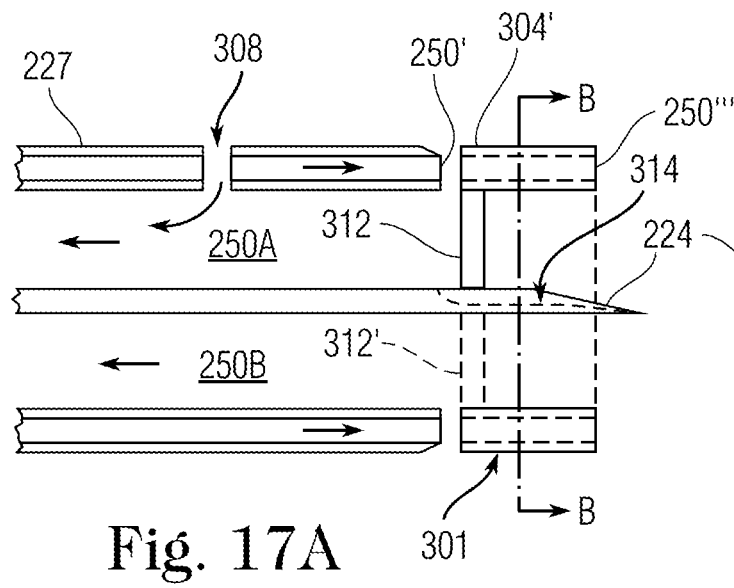
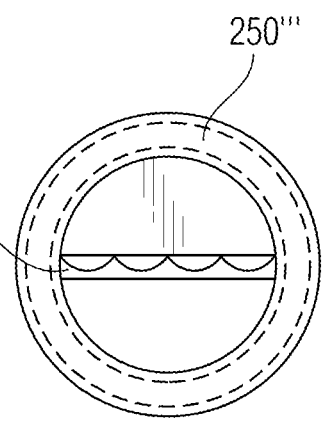
Fig. 17A    Fig. 17B
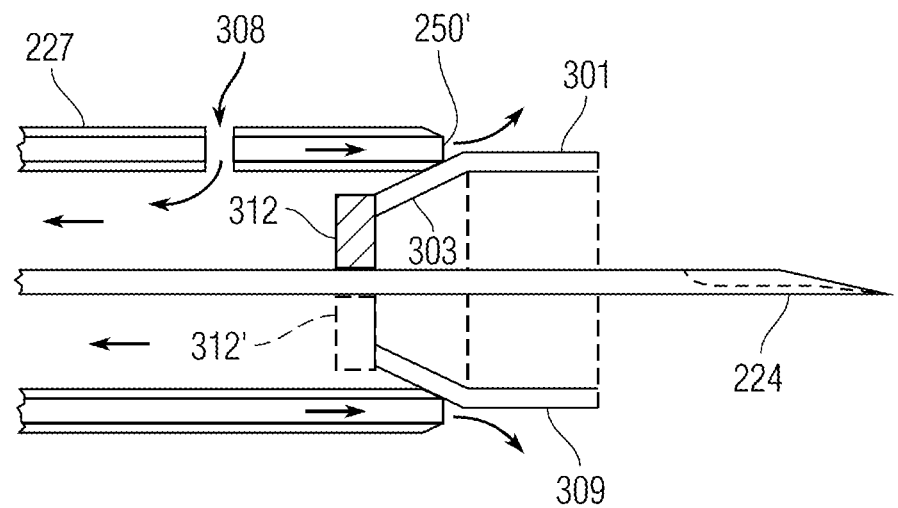
Fig. 18

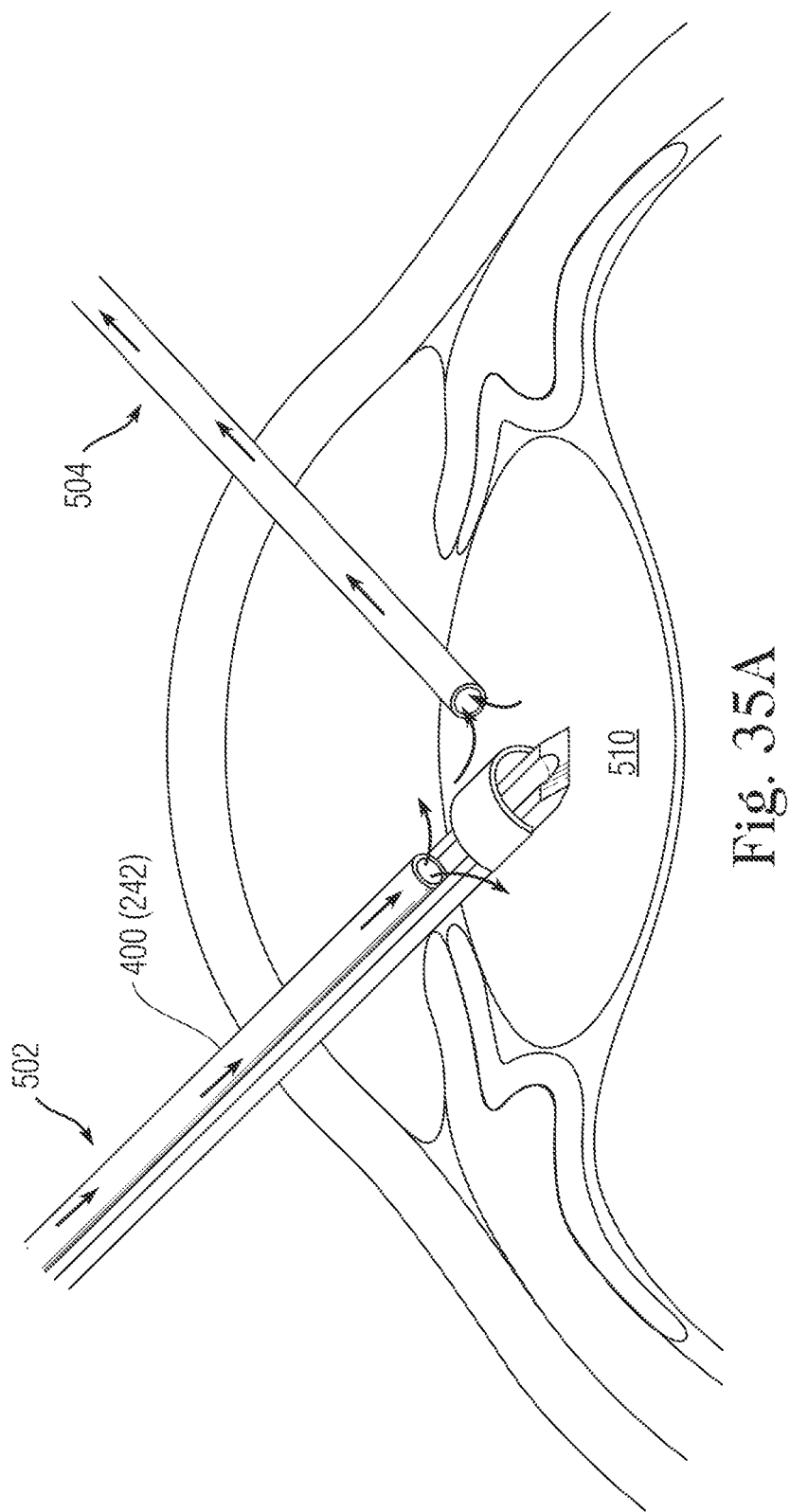
Fig. 35A
Fig. 35B
Fig. 35C

SURGICAL HAND PIECE WITH POST-OCCLUSION SURGE ELIMINATION

The present invention is a continuation-in-part of U.S. patent application Ser. No. 15/941,366 filed Mar. 30, 2018, the contents of which are incorporated herein by reference in their entirety.

TECHNICAL FIELD

The present invention is generally directed to work tips for surgical hand pieces, particularly work tips with cone shapes for use in the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIGS. 1A and 1B show a work tip for a prior art ultrasonic hand piece as shown in U.S. patent application Ser. No. 15/783,806 filed Oct. 13, 2017 for Dr. William Banko, the present inventor. This design has a handpiece 200 with an ultrasonic vibration part 210 connected to a work tip 220. The vibration part has a housing 214. A transducer 212 is provided in part 210 for generating ultrasonic linear mechanical vibrations upon excitation with an alternating-current electrical signal. The transducer is supported within the housing 214 by flanges 211. A metal connecting body 216 having a reduced diameter distal end portion is attached to the transducer 212. The connecting body forms an acoustic impedance transformer for conveying the longitudinal vibrations of the transducer 212 for application to the operative working tip 220 connected to the distal end of the connecting body 216. Further, the housing has a part 213 that engages the connecting body 216 at a null point in its vibration to provide further support.

The work tip 220 has a hub 222 connected to the distal end of the connecting body 216. The distal end of the hub narrows down to form a solid blade, knife or scalpel 224. Flexible tube 230 extracts aspiration fluid from a rigid plastic tube 250 that is located along the blade 224 in the assembled condition. Similarly, a flexible tube 242 provides irrigation fluid to a rigid plastic tube 250' that is located along the blade 224.

A sterile sheet 232 surrounds the vibration part 210, housing 214 and connecting body 216 to isolate them from the non-sterile conditions at the work tip 220. In this design the sheet 232 is attached to the hub 222 of the knife which is detachable from the connecting piece 216. As a result, after an operation the hub can be detached from the work piece and it, the knife and the sheet can be discarded as a one-use product. Since the vibration part 210, housing 214 and connecting body 216 did not come into contact with any tissue or fluids from the last patient and will not contact the tissue or fluids from the next patient, there is no need to sterilize these elements between operations on different patients. As a result, multiple operations can be conducted in a shorter period of time and at less expense.

Rigid tubes 250, 250' are captured in tube holders 240, 240' with the sterile sheet between them. That is, the holders are within the sheet and are not exposed to the operating environment. As shown in FIG. 1B there is a sleeve 226" around the blade 224. This sleeve has channels 250, 250' which are extensions of the plastic tubes 250, 250.' The space 225 for the blade 224 is adjacent to the channels so the blade is adjacent to the fluid channels but does not touch them. Further, sleeve 226" includes a third channel 282 that is located on the side of the work pieces while the irrigation tube 250' is on the top and aspiration tube 250 is on the bottom. The tubes are all located on sleeve 226". The proximal end of the blade channel 225 is blocked by an O-ring 223 so that fluid from the operating site does not pass through this channel of the work tip.

During an operation, the hub 222 and blade 224 of work tip 220 are longitudinally vibrated by the transducer 212. The tubes 250, 250' remain stationary and are supported with respect to the hub and knife by means of the O-ring 223 at the interface between the hub and the tubes. The surgeon places the work tip 220 within the eye and against the cataract tissue. The ultrasonic vibration of the blade 224 causes the cataract tissue to emulsify. During this process irrigation fluid, e.g., saline solution, is injected into the site from tube/channel 250' since flexible tube 242 is connected to a source of irrigation fluid which may be moved by gravity flow or a pump. Also, the emulsified tissue is removed from the site by aspiration through tube/channel 250 because flexible tube 230 is attached to an aspiration pump. The tube 282 can be used to assist either the irrigation or aspiration flow.

In FIG. 1B the aspiration channel 250 is small compared to the irrigation channel 250'. This can be balanced out using channel 282 to augment aspiration. During an A/I clean up procedure after the cataract has been broken up into little pieces, a low aspiration force is needed to remove the remaining pieces of lens and lens epithelial cells while preventing the tearing of the capsular bag of the eye. Under those circumstances the channel 282 can be closed or used to augment irrigation so that aspiration only occurs though channel 250.

The cross section shown in FIG. 1B has the channel 282 protruding from one side of sleeve 226". Since this structure is required to pass through an incision in the eye, it would be beneficial if the cross section were more uniform but provided the same functional benefits.

Further, there is a prior art work tip known as the "Cobra" tip that has a cone shape. In particular, a cylindrical work tip has an area in which its diameter is increased going from the proximal to the distal end. An early discussion of this tip can be found in the article "New Phaco Tip Geometry Balances Power, Suction," *Ophthalmology Times*, Jul. 15, 1992, Vol. 17, No. 14. As reported in the article the shape concentrates ultrasonic energy within the tip, improving safety and efficiency. In effect the sloped walls of the cone shape provide additional force when the tip is vibrated at ultrasonic rates. See also, the article "Funnel-shaped tip Controls Ultrasound Energy during Phaco," *Ocular Surgery News*, Jul. 1, 1992, Vol. 10, No. 13. It would also be beneficial if the enhanced performance of the Cobra tip could be incorporated into more modern work tips.

SUMMARY OF THE INVENTION

In accordance with the invention a surgical hand piece is provided with a solid ultrasonic blade, knife or scalpel located in a sleeve with multiple fluid channels, while retaining a uniform cross section. Further, a cobra cone shape is incorporated into the distal end of the knife to improve its efficiency In an illustrative embodiment the surgical hand piece has a solid blade located within a circular sleeve. The sleeve provides irrigation and aspiration channels. Further, the blade may be in its own channel and may be used to divide that channel into separate irrigation and aspiration fluid flows.

A cone shape may be included at the distal end of the blade. This cone shape in one embodiment interacts with the structure within the sleeve so that in an extended state the work tip performs phacoemulsification, while in a retracted state the aspiration fluid flow path is altered to reduce the flow so that the same work tip can be used for irrigation/aspiration (I/A) cleanup.

In another embodiment, the cone shape tip can be replaced with a cap shape that is open toward the distal side, which generates greater phacoemulsification energy than the cone shape.

A further embodiment has a work tip extending from a sleeve, where a portion of the work tip is in the form of a structure with a half cylindrical main part and a half hemispherical distal end. This structure is provided on the upper surface of a blade. The distal end of the structure has an aspiration cleanup hole in it. During phacoemulsification the blade engages the cataract, irrigation fluid flows out of the sleeve over the upper surface of the blade and around the attachment. Aspiration fluid flows through a collar located under the blade and into the sleeve. During cleanup, the work tip is withdrawn into the sleeve and fluid flow is reversed. In particular, aspiration occurs only through the cleanup hole in the hemispherical distal end and into the sleeve above the blade. Irrigation fluid passes out of the sleeve under the blade and through the collar.

In a still further embodiment, a groove is provided in the hub and/or blade of the work tip to accommodate an infusion tube that provides fluid to the operating site. An aspiration tube is provided below the blade. In the other embodiments there is a single tube surrounding the blade with aspiration on top of the blade and irrigation below. This embodiment, however, eliminates connectors at the distal end of the work piece that are required with the other embodiment, thus providing a simpler, less expensive design.

The principles of the invention have numerous advantages. For example, the invention allows for a work tip that is easier to insert into an incision in the eye, but still provides multiple fluid flow paths for use in phacoemulsification and cleanup procedures. It also provides a cone shape to improve the efficiency of the ultrasonic vibrations. By causing the cone shape to interact with a structure in a surrounding sleeve, the work tip function can be changed from phacoemulsification to cleanup without having to remove the work piece from the surgical site, such as the eye, and to replace it with an irrigation/aspiration (I/A) cleanup tool. Further, according to the present invention, cleanup can be commenced without the surgeon having to divert his attention from the eye of the patient.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIGS. 1A and 1B are a side view and a cross-sectional view, respectively, of a prior art surgical hand piece with irrigation, aspiration and a third fluid flow path that can be used to augment either of the other two paths;

FIG. 4A is a right-side perspective view of the sleeve with an internal structure and hole near its distal end according to an embodiment of the present invention, FIG. 4B is a front elevation view of the sleeve and structure of FIG. 4A and FIG. 4C is a right-side cross-sectional view of the sleeve and structure of FIG. 4A;

FIG. 17A is a side view of an arrangement similar to FIG. 11 but with a full ring and showing the blade surrounded by a sleeve with fluid irrigation channels and a radial blocking structure in the tip, and FIG. 17B is a front cross-sectional view along line B-B of the structure of FIG. 17A with the structure in the tip blocking the upper channel.

FIG. 18 is a side view of the structure similar to that of FIGS. 13 and 14 showing the blade and a structure within the sleeve blocking the proximal end of the cone shape;

FIG. 35A illustrates a phacoemulsification procedure using a second instrument, FIG. 35B shows the lumen of the second instrument when used for either aspiration or irrigation, and FIG. 35C shows the lumen of the second instrument when used for both aspiration and irrigation.

DETAILED DESCRIPTION OF THE INVENTION

Figure 2:
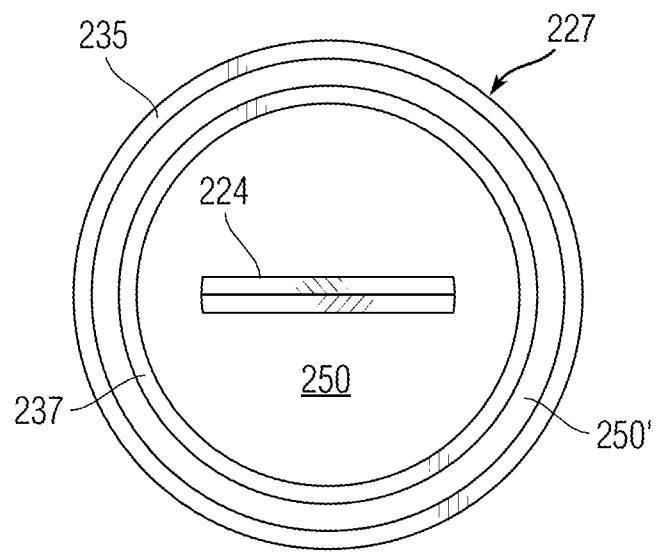
FIG. 2. is cross-sectional view of a blade within an inner channel of a work tip sleeve and a surrounding outer channel according to an embodiment of the present invention.

FIG. 2 shows an external sleeve 227 in the form of two concentric tubes 235, 237. The blade 224 is in the center of channel 250 but does not extend completely across the tube 237. With this arrangement irrigation fluid can flow in the channel 250' between the tubes, while aspiration fluid can flow in channel 250 within tube 237.

Figure 3:
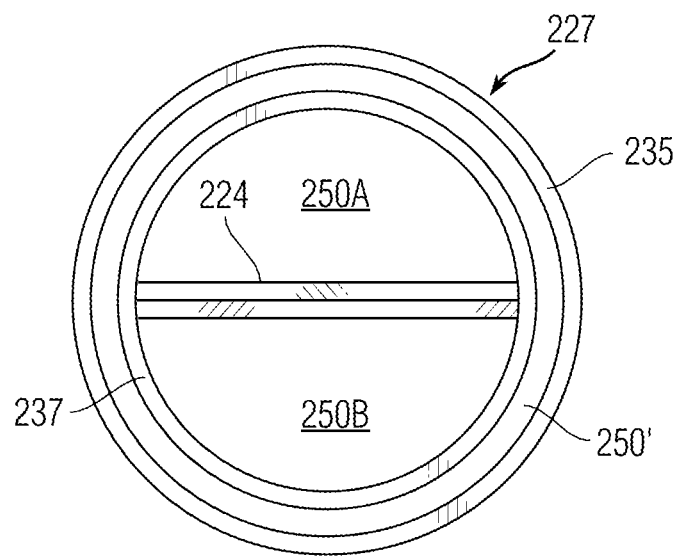
FIG. 3 is a cross-sectional view of a modification of the design of FIG. 2 in which the blade extends completely across the inner channel and divides it into upper and lower channels.

In FIG. 3 the blade 224 extends completely across tube 237 and separates the channel 250 into two distinct chambers, 250A and 250B. Again, the irrigation is in channel 250' between tubes 235, 237. However, because channel 250 has been divided into two channels, there are a total of three channels available that can be alternated or switched by the operation to change the performance. For example, the arrangement can have two aspiration channels and one irrigation channel, or one aspiration channel and two irrigation channels. It should be noted that in FIGS. 2 and 3 the sleeve 227 has a round shape which will make it easier for the surgeon to pass it into an incision in the patient's eye. In particular, it does not have a protrusion like channel 282 in FIG. 1B.

In FIG. 4A there is shown a small hole 308 in a single wall sleeve 227'. Because this sleeve has only a single wall, it cannot provide an outer irrigation channel. Instead, the single channel will need to be divided into irrigation and aspiration channels. As will be described in more detail below, the hole 308 can be used as the aspiration opening during cleanup. A structure 306 is shown suspended in the end of sleeve 227' in the upper part. The shape of the structure is best seen in FIG. 4B. Also, the location of the structure with regard to the hole 308 can be determined in FIG. 4C.

Figure 5:
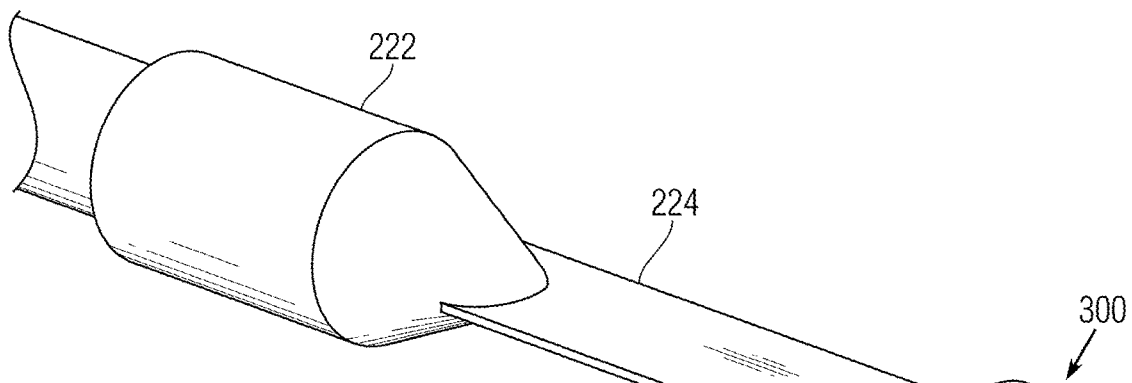
FIG. 5 is a perspective view of the connecting piece attached to a knife blade having a half conical structure at its distal end according to an embodiment of the present invention.
Figure 6:
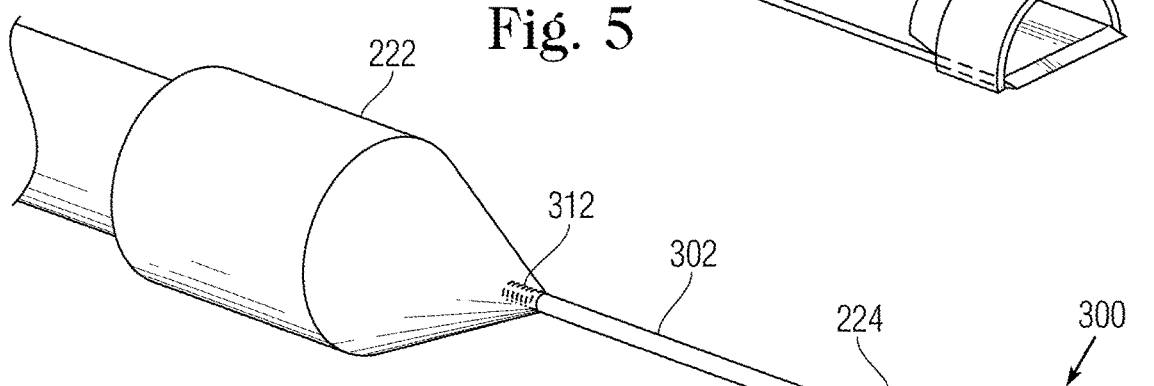
FIG. 6 is a perspective view of the connecting piece attached to a rod leading to the knife blade, which has a half conical structure at its distal end according to an embodiment of the present invention.
Figure 9:
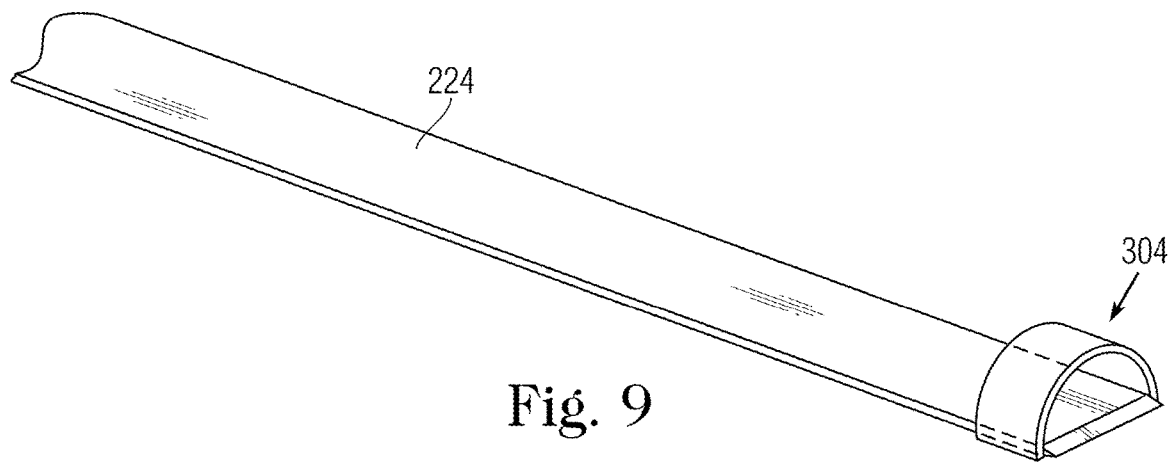
FIG. 9 a perspective view of a knife blade having a half ring structure at its distal end, but without showing a connecting piece according to an embodiment of the present invention.
Figure 10:
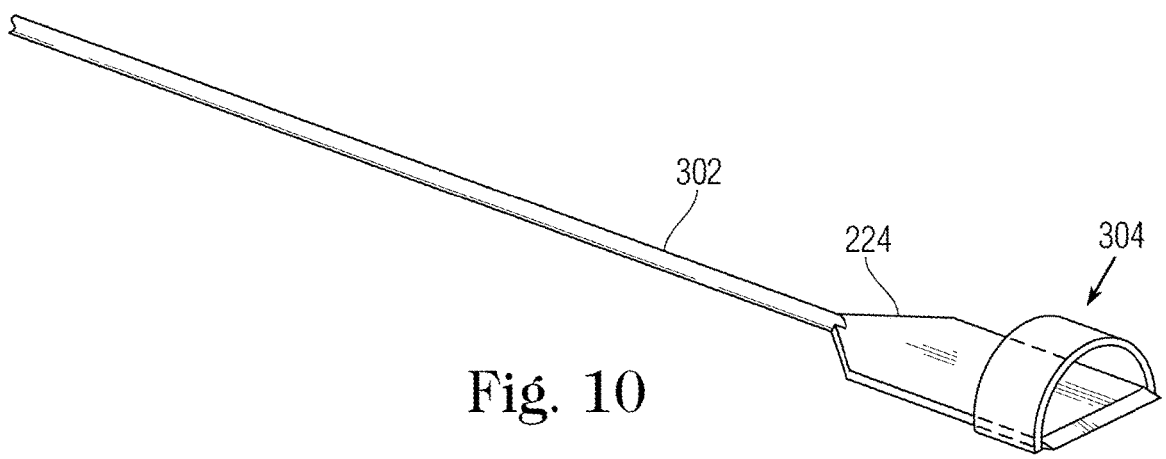
FIG. 10 is a perspective view of a rod attached to a knife blade that has a half ring structure at its distal end, but without showing a connecting piece according to an embodiment of the present invention.
Figure 11:
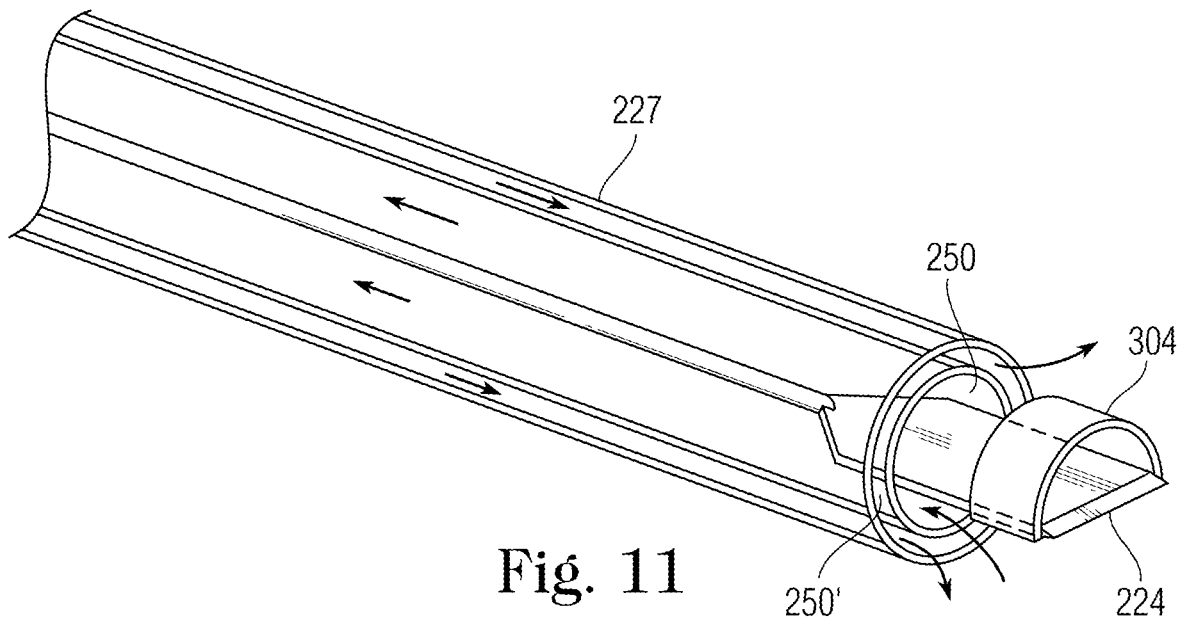
FIG. 11 is a perspective view of the distal end of a sleeve with irrigation and aspiration channels surrounding a rod with a knife blade at its end having a half ring or collar according to an embodiment of the present invention.

The double wall sleeve 227 of FIGS. 2 and 3 or the single wall 227' of FIGS. 4A-4C is designed to be used with one of the knives shown in FIGS. 5-10, as shown, for example in FIG. 11. FIG. 5 shows a connecting body or hub 222 with a knife or blade 224 extending from it. At the distal end of the knife there is a half Cobra tip 300, i.e., a cylindrical body with a conical shape at its proximal end. FIG. 6 shows the connecting body or hub 222 and a rod 302 extending form it to a portion of a blade 224. The connecting body and the rod are fixed to each other by a threaded connection 312. The distal end of the knife has half Cobra tip 300 fastened to it. The rod and connecting body or hub may be formed as one piece to lower the cost of machining the part. As an alternative the rod and/or blade may screw into the connecting body.

Figure 7:
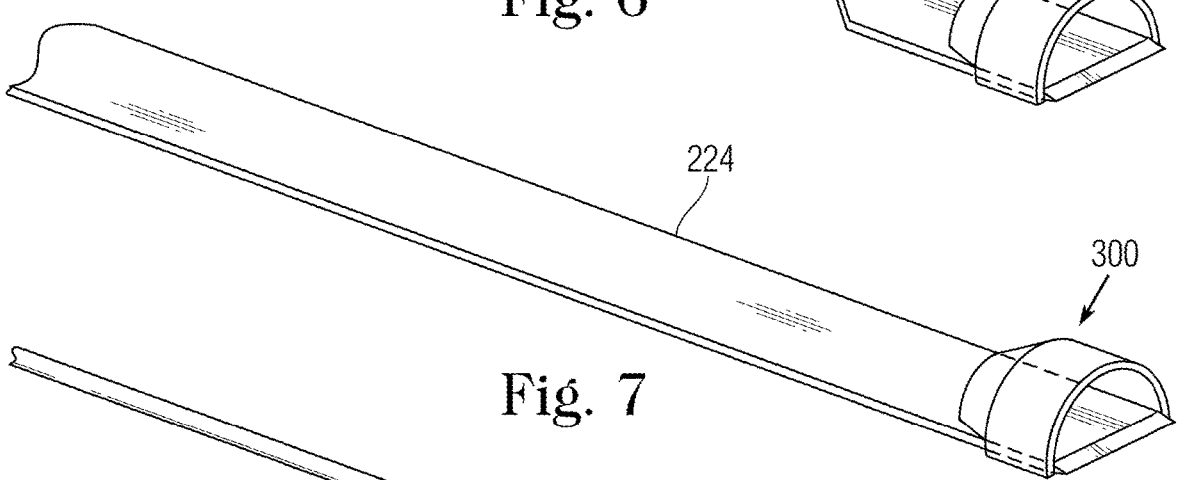
FIG. 7 is a perspective view of a knife blade having a half conical structure at its distal end, but without showing a connecting piece according to an embodiment of the present invention.
Figure 8:
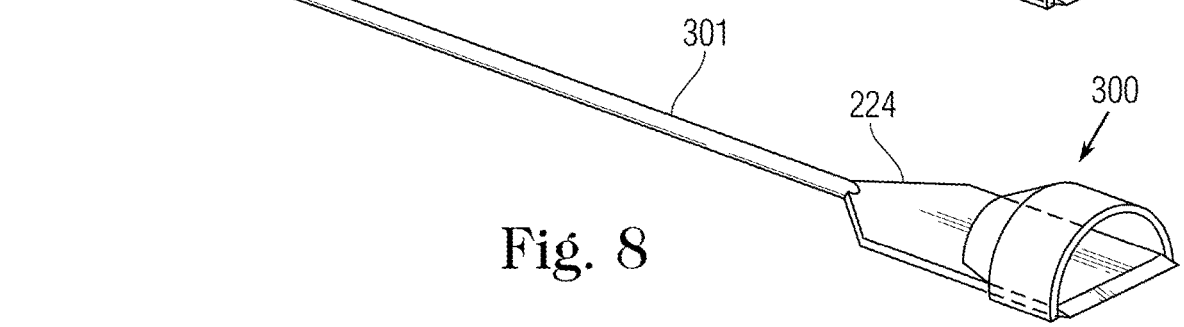
FIG. 8 is a perspective view of a rod attached to a knife blade that has a half conical structure at its distal end, but without showing a connecting piece according to an embodiment of the present invention.

The design of FIG. 7 is similar to that of FIG. 5, but without the connecting body or hub. The design of FIG. 8 is similar to that of FIG. 6, but without the connecting body or hub. In FIG. 9 the design is like that of FIG. 7, but the half Cobra 300 is replaced with a half ring (collar) 304. In like fashion, the design of FIG. 10 is similar to that of FIG. 8, but with a half ring or collar 304.

In FIG. 11 the blade 224 of FIG. 10 is shown installed in the double-walled sleeve 227 of FIG. 3. The blade is vibrated at ultrasonic frequencies to break up the cataract. During this process irrigation fluid is directed to the surgical site through channel 250'. The emulsified tissue is withdrawn though channel 250, which also contains the knife. Note that the distal end of the knife has a shape edge for breaking the cataract. In addition, the distal edge of the collar 304 also impacts the cataract and assists in phacoemulsification.

Figure 12:
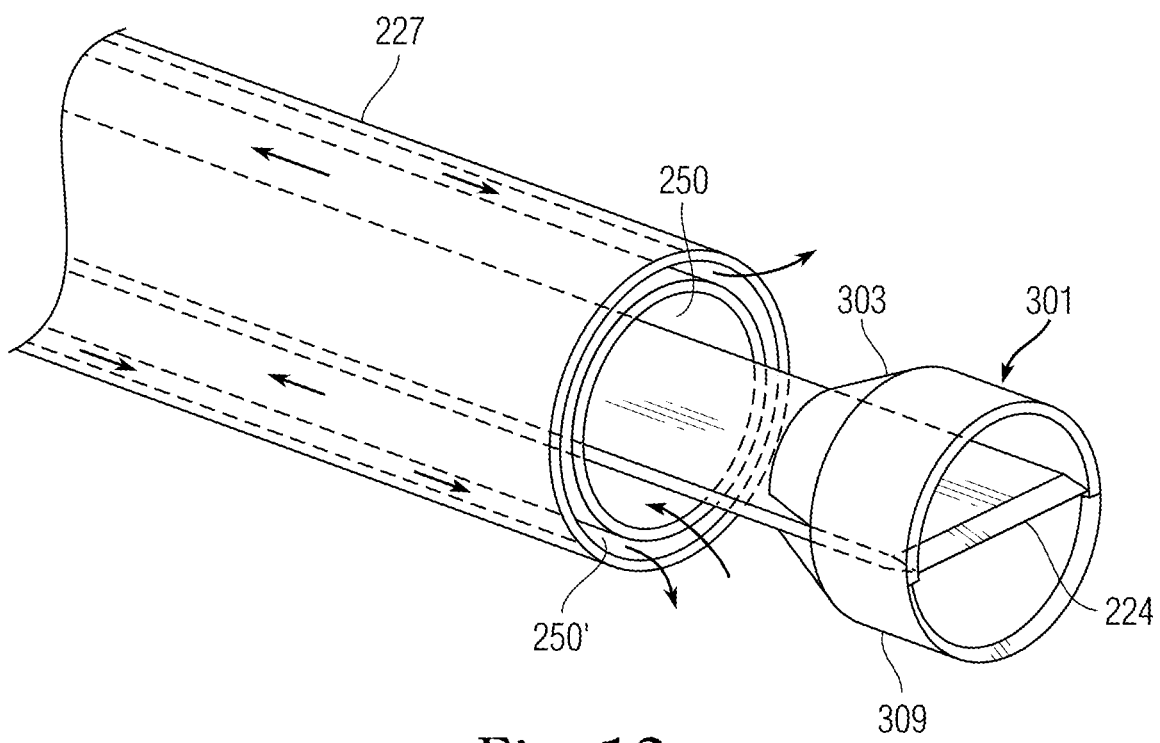
FIG. 12 is a perspective view of the distal end of a sleeve with irrigation and aspiration channels surrounding a knife blade with a full conical structure at its end according to an embodiment of the present invention.

The arrangement of FIG. 12 has blade 224 with a full Cobra tip 301 at its distal end. This knife is positioned in the sleeve 227 of FIG. 3. Generally, the design of FIG. 12 operates similar to that of FIG. 11. However, the full Cobra tip 301 increases the force generated by the ultrasonic vibrations. In particular, the conical shape 303 of the Cobra tip causes fluid to be pushed toward the surgical site. Also, note that in FIG. 11, aspiration fluid can be drawn into channel 250 both above and below the knife, and in particular under the ring 304. In the design of FIG. 12 if the cylindrical part 309 of the Cobra tip 301 has a diameter similar to the diameter of channel 250', no or at least a limited amount of irrigation fluid can pass from this channel, but aspiration fluid can flow though the full Cobra tip to enters the channel 250 after the tip. Since irrigation is important, the diameter should not be made large enough to limit irrigation flow.

Figure 13:
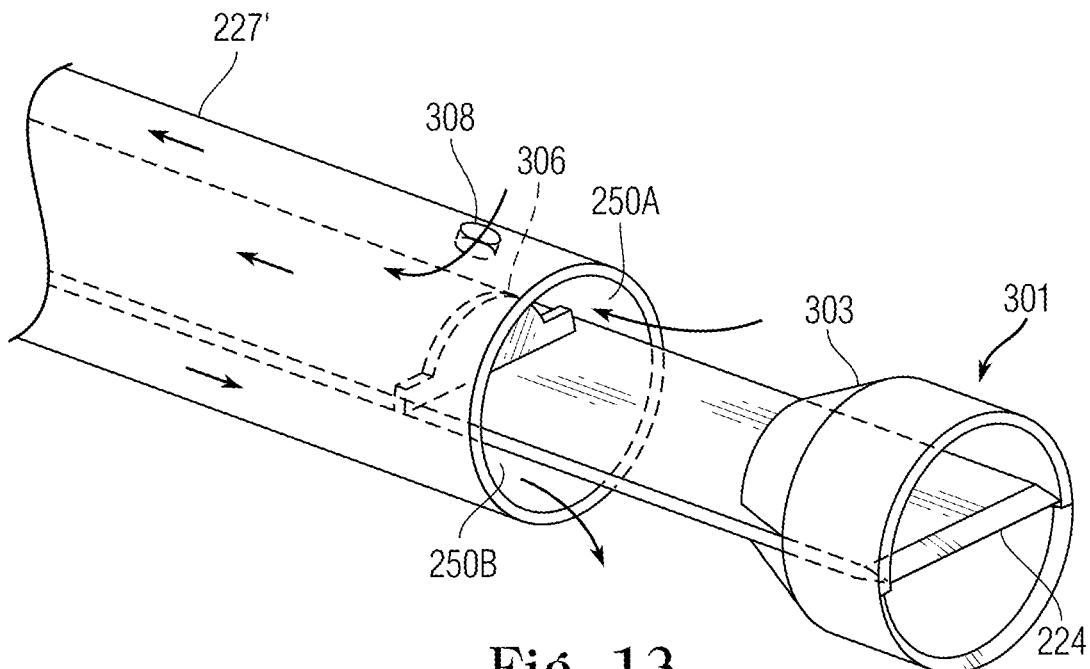
FIG. 13 is a perspective view of the distal end of a sleeve surrounding a knife blade in an extended state, a full conical structure at the end of the knife and a structure in the sleeve for changing the operation of the work tip according to an embodiment of the present invention.
Figure 14:
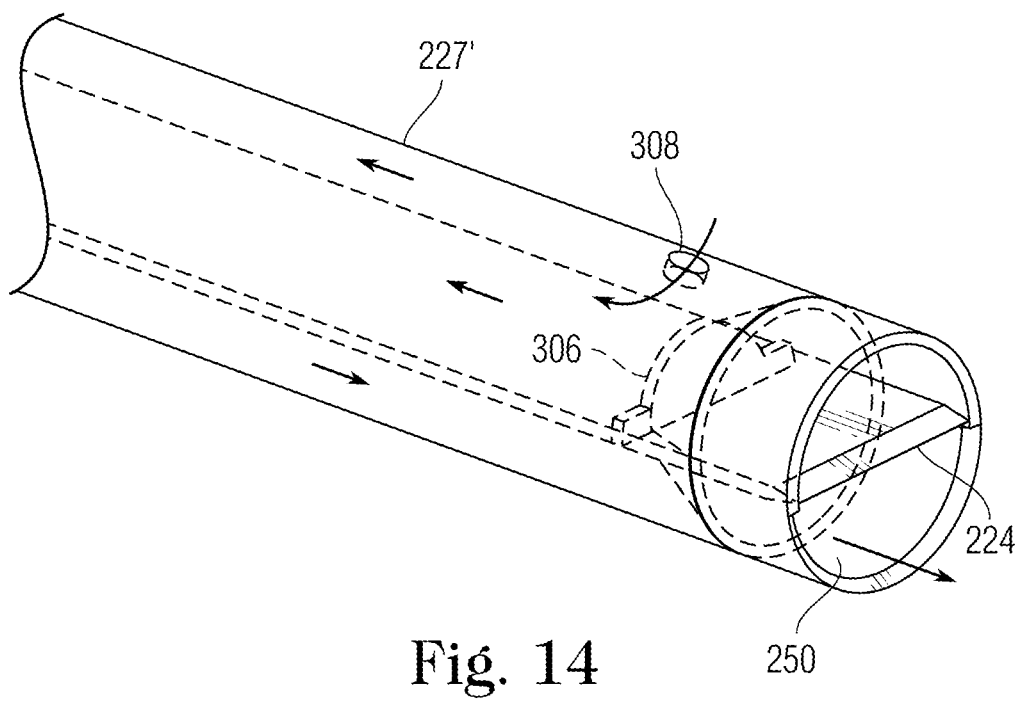
FIG. 14 is a perspective view of the arrangement of FIG. 13 with the knife in a retracted position.

In FIG. 13 there is shown the same knife as in FIG. 12, but the sleeve 227' is a single wall sleeve like that shown in FIGS. 4A-4C. The upper surface of the blade 224 slides under the bottom surface of the structure 306, which is in the distal end of sleeve 227'. The blade has a full Cobra tip 301 at its end. The conical wall 303 of the full Cobra tip forms an opening at the proximal end of the tip. The shape of this opening matches the shape of the structure 306 so that when the knife is withdrawn into the sleeve as shown in FIG. 14, the structure 306 blocks the portion of the opening at the proximal end of the tip that is located above the knife. The part of that opening below the blade is not blocked. As a result, irrigation fluid in the channel 250B can flow to the surgical site both when the knife is extended and when it is retracted.

The design shown in FIG. 13 with the knife extended is what is used for phacoemulsification. Aspiration fluid is withdrawn from the surgical site around and through the tip 301 and into the channel 250A above the knife. Also, a small amount of aspiration fluid flows through hole 308. When the tip is used for cleanup, the blade 224 is withdrawn into the sleeve 227'. The aspiration flow over the top of blade 224 and into chamber 250A becomes blocked by the structure 306, so the only path for aspiration is the reduced path through hole 308. Irrigation flow, however, can continue to flow through channel 250B.

Figure 15:
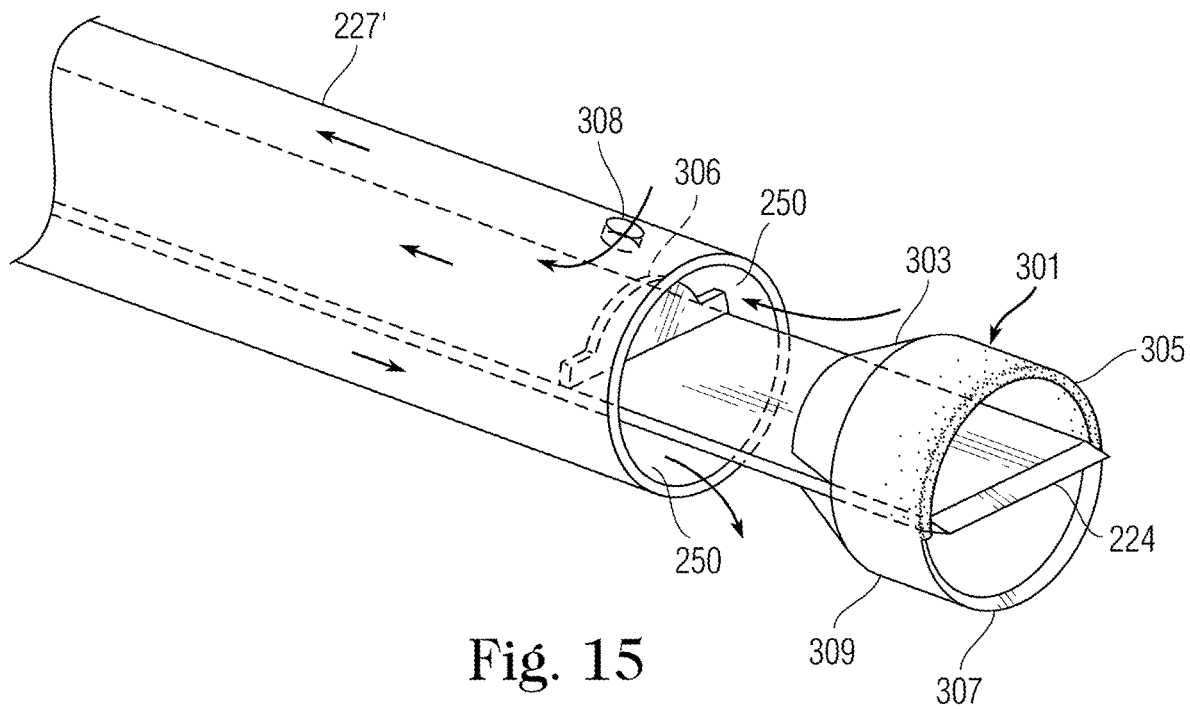
FIG. 15 is a perspective view of the arrangement of FIG. 13, but with an upper portion of the distal end of conical shape having a rounded textured surface and the lower portion being in the form of a sharp cutting edge.

FIG. 15 shows the same arrangement as FIG. 13, but an upper portion 305 of the distal end of the conical shape has a rounded textured surface and the lower portion 307 is in the form of a sharp cutting edge. The texturing of surface 305 can be achieved by several methods, for example by sand blasting. This textured surface is used to scrape the epithelial cells form the posterior capsule during the I/A procedure. The bottom half of the work tip with the sharp edge is used to cut the cataract.

Figure 16:
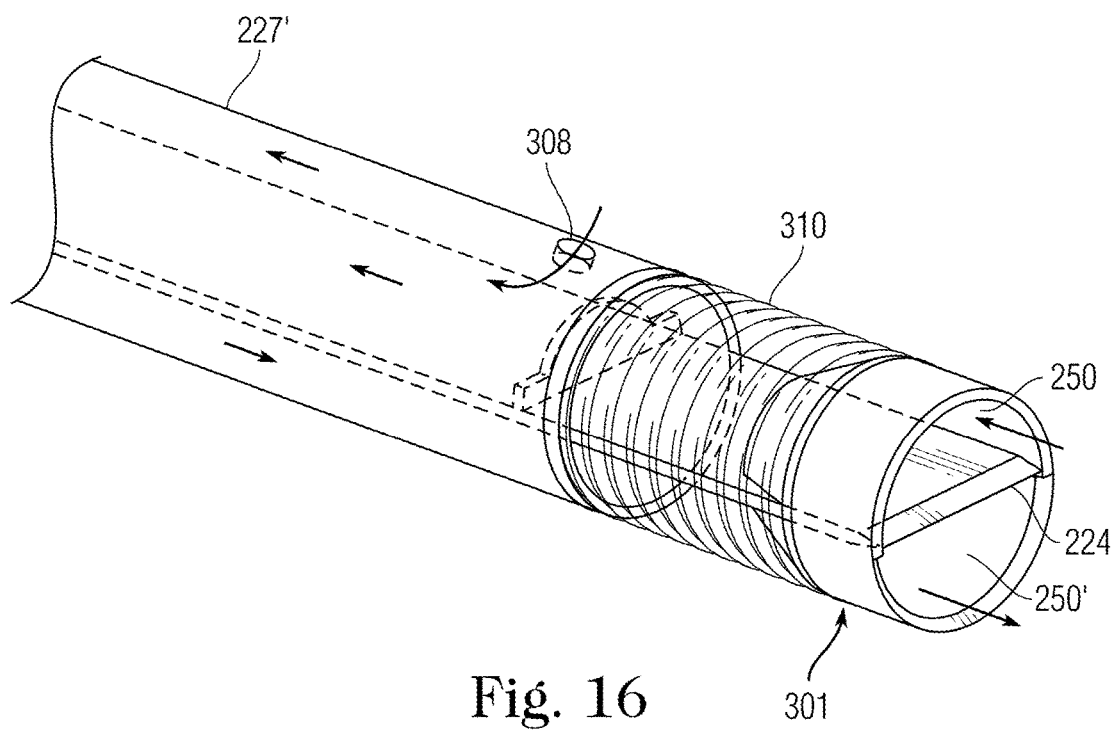
FIG. 16 is a perspective view of the arrangement of FIG. 13 further including a protective sheath between the distal end of the sleeve and the expanded part of the conical shape.

FIG. 16 shows the same perspective view of the work tip as shown in FIG. 13; but, equipped with a protective sheath 310 provided between the distal end of the sleeve 227' and the expanded or cylindrical part 309 of the conical/Cobra shape 301. Because of the sheath 310 fluid cannot flow around the Cobra tip but must go through the Cobra tip. The sheath can be thin, flexible and transparent.

A side view of the arrangement of FIG. 11 with a collar 304 at the work tip is shown in FIG. 17A. A front cross-sectional view of this arrangement is shown in FIG. 17B. Unlike the structure of FIG. 11, in FIG. 17A the collar 304 extends completely around the blade 224, i.e., it is full collar 304'. Further, like the arrangement in FIG. 15, there is a structure 312 that blocks the channel 250A above the knife when the knife is retracted into the sleeve 227. However, the structure 312 is located at the proximal end of the collar and not within the sleeve. When the knife is extended, and a phacoemulsification operation is begun, the ultrasonic vibration of the collar breaks up the cataract. In addition, the vibration of wall 312 causes fluid cavitation that assists in breaking up the cataract. This perpendicular wall 312 is even more efficient in this respect than the conical wall 303 of a standard Cobra tip. The irrigation flow is in channel 250' during phacoemulsification and aspiration can be through channels 250A and 250B. During clean up, depending on the structure of collar 304', it can either block irrigation flow when the knife is fully retracted, or the collar can be provided with an extension of the channel 250'" so that irrigation fluid continues to reach the surgical site during clean up when the knife is retracted into the sleeve. In the fully retracted position the wall 312 blocks aspiration channel 250A, which tends to cause more aspiration to occur through hole 308, which can be ideal for cleanup. A similar wall 312' shown in dotted line can be provided on the tip 304' below the knife so as to block channel 250B and cause all of the aspiration to occur through hole 308.

FIG. 18 shows a side view of a schematic arrangement like that in FIG. 17A, but with a Cobra tip 301 instead of the collar 304. FIG. 18 shows the knife in the retracted position in which the opening at the proximal end of the conical surface 303 is blocked by the structure 312. As an option in this arrangement as well as in the arrangement of FIG. 17A, the cylindrical portion of the tip is smaller in diameter than the channel 250' so that even in the retracted position irrigation fluid can flow from channel 250'.

Figure 19:
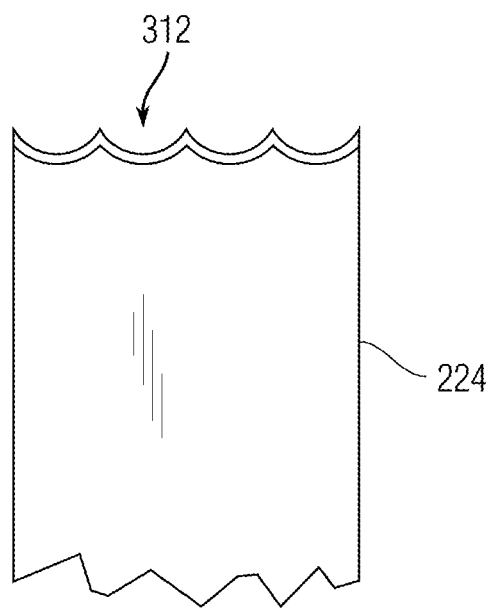
FIG. 19 is a plan view of a knife according to the present invention with a serrated edge.
Figure 20A:
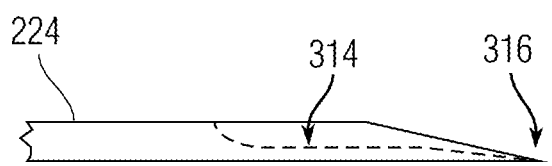
FIGS. 20A and 20B are side and plan views of a knife according to the present invention with scalloped edges.
Figure 20B:
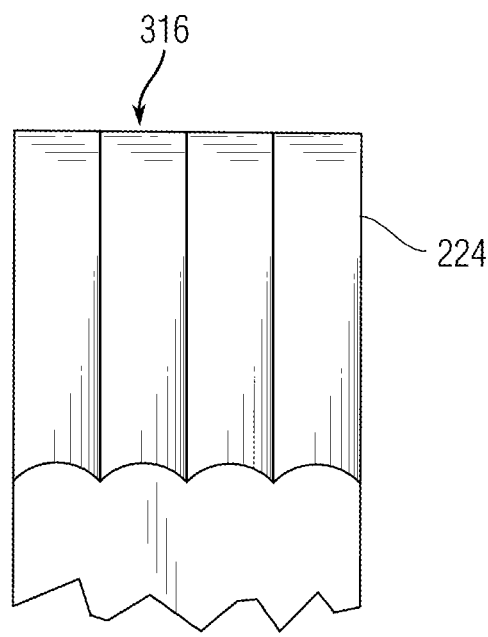

The end of the blade 224 in FIG. 18 shows a scooped portion in dotted line that is shown in side view in FIG. 20A and plan view in FIG. 20B. FIG. 19 is a plan view of the blade 224 with a serrated edge. This shape helps in the cutting of the cataract. As indicated FIGS. 20A and 20B are side and plan views of the blade 224 with scalloped edges. These edges also help with the cutting of the cataract.

Figure 21A:
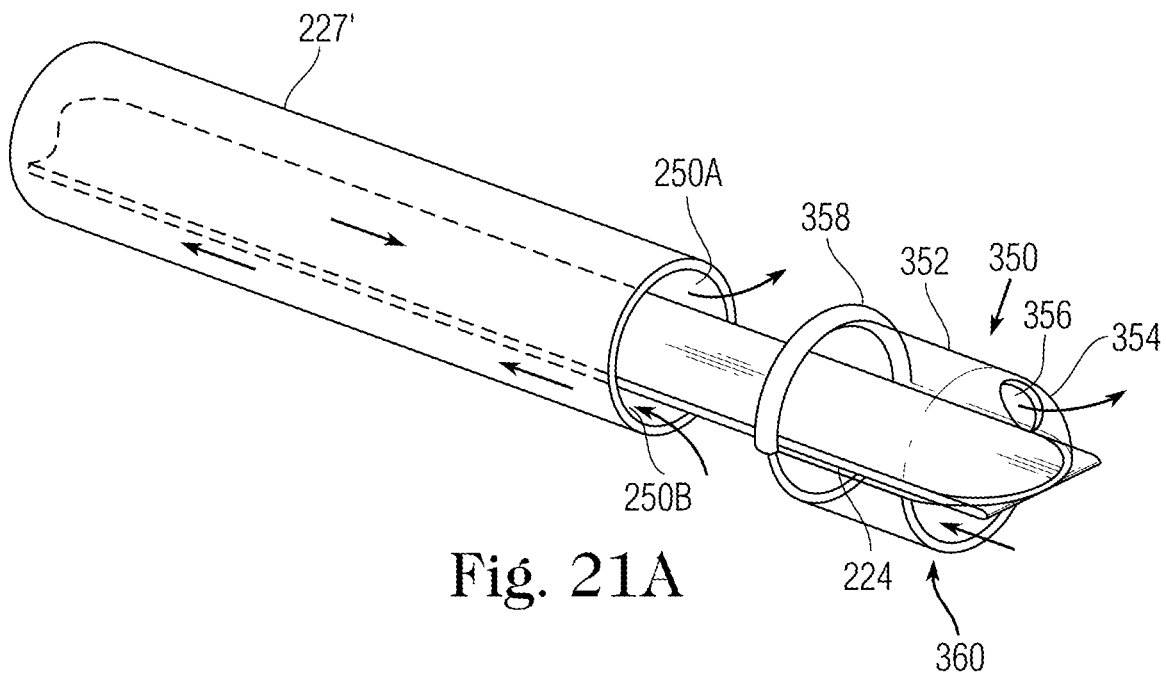
FIG. 21A is a perspective view of an embodiment with a work tip in the form of a half cylindrical/hemispherical structure on top of a blade and a collar below the blade, with the work tip in an extended position with regard to a sleeve.
Figure 21B:
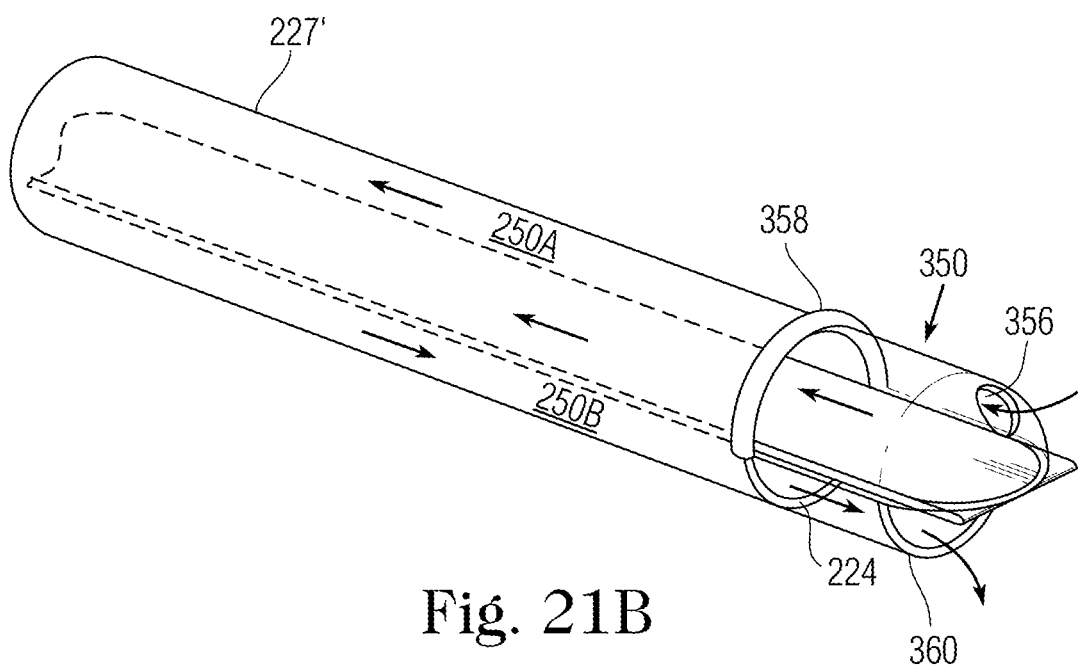
FIG. 21B is a perspective view of the embodiment of FIG. 21A in the retracted position.

FIGS. 21A and 21B show an embodiment with a work tip in the form of blade 224 that has a half cylindrical/hemispherical structure 350 on the upper surface of the blade. A half collar 360 is located on the lower surface of the blade at about the location of the half cylindrical/hemispherical structure 350. The structure 350 includes a half cylindrical part 352 and a half hemispherical part 354 that is on the distal end of the part 352. The part 354 has an aspiration hole 356. The proximal portion of the half cylindrical part 352 has a sealing member 358. During phacoemulsification, it is the distal edge of the collar 360 that scoops out or cuts the cataract. During cleanup, the instrument is turned over so only the smooth surface with the aspiration opening 356 that contacts the ocular sack.

The position shown in FIG. 21A has the work tip extended from the single walled sleeve 227'. If additional fluid flow arrangements were of interest, sleeve 227' could be replaced with a double walled sleeve 227 where fluid flow would exist between the walls as shown in FIG. 3. The embodiment of FIG. 21 is used for phacoemulsification when in the extended position of FIG. 21A. The portion of collar 360 below the blade 224 engages a cataract (not shown) while being vibrated at an ultrasonic frequency. This causes the cataract to break up into small pieces. During this time irrigation fluid passes through the sleeve from the hand piece (not shown) in the space 250A above the blade 224. It can exit the space between the distal end of the sleeve 227' and the structure 350, and flow around that structure to the surgical site. A portion of the irrigation fluid can also pass through hole 356 in structure 350 to the surgical site.

During phacoemulsification, the small pieces of cataract are aspirated by fluid flow into the sleeve through the space 250B. Pieces are drawn directly from the surgical site through the collar 360 and into the space 250B. In addition, some fluid is drawn from the space between the half cylindrical/hemispherical structure 350 and the distal end of the sleeve.

When it is time for irrigation/aspiration (I/A) cleanup of remaining epithelial cells on the capsular sack, the ultrasonic vibration may be reduced or turned off. Also, the work tip is withdrawn so that seal 358 engages the distal end of the sleeve above the blade as shown in FIG. 21B and closes off the flow of fluid above the blade and between the sleeve and work tip. In this state the fluid flow is reversed so that aspiration flow is set up in channel 250A. Thus, at the surgical site, aspiration occurs only through hole 356 on the rounded surface 354. This is much like a separate conventional I/A tool, but is part of a phacoemulsification tool, so 2 in 1 functionality is provided. During this I/A procedure, irrigation fluid is passed through channel 250B of the sleeve 227' below the blade 224, and through the collar 360 to the site of the cleanup.

The reversal of fluid flow can be by way of valves in the hand piece or the control apparatus as is well known in the art.

The work tip of FIGS. 21A & B can be made of metal, for example titanium. As an alternative, the half cylindrical/hemispherical structure 350 could be made of hard plastic or even some composite material that will withstand ultrasonic vibration, while the seal 358 is made of an elastomeric material.

Figure 22A:
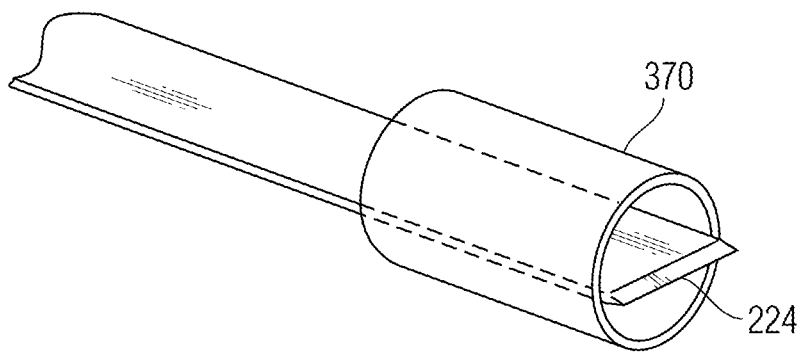
FIG. 22A shows a work tip with a full collar surrounding a blade.
Figure 22B:
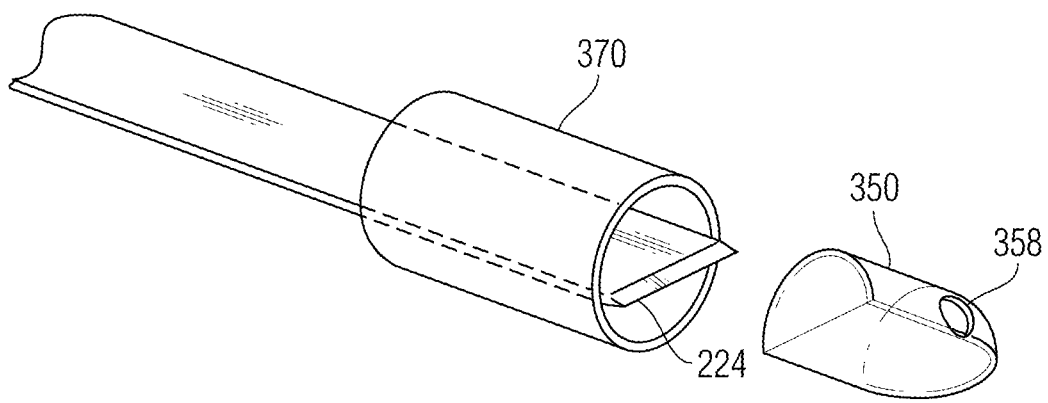
FIG. 22B shows a half cylindrical/hemispherical insert that fits in the collar of the work tip of FIG. 22A above the blade.
Figure 22C:
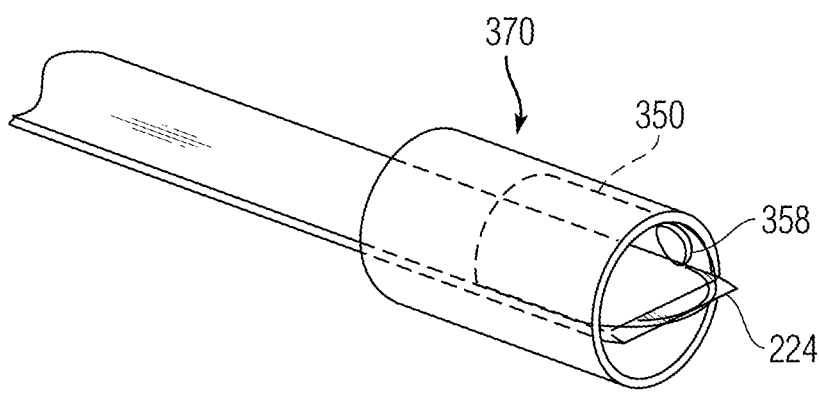
FIG. 22C shows the insert in position in the collar for operation according to the embodiments of FIG. 21.

FIG. 22A shows a work tip with a full collar 370 surrounding a blade 224. FIG. 22B shows the half cylindrical/hemispherical structure as a separate insert 350. This insert is adapted to fit in the collar 370 and be attached to the upper surface of the blade 224. FIG. 22C shows the insert 350 in position in the collar 370. When assembled in this way, the work tip of FIG. 22C can be operated like the embodiments of FIG. 21 discussed above.

Figure 23:
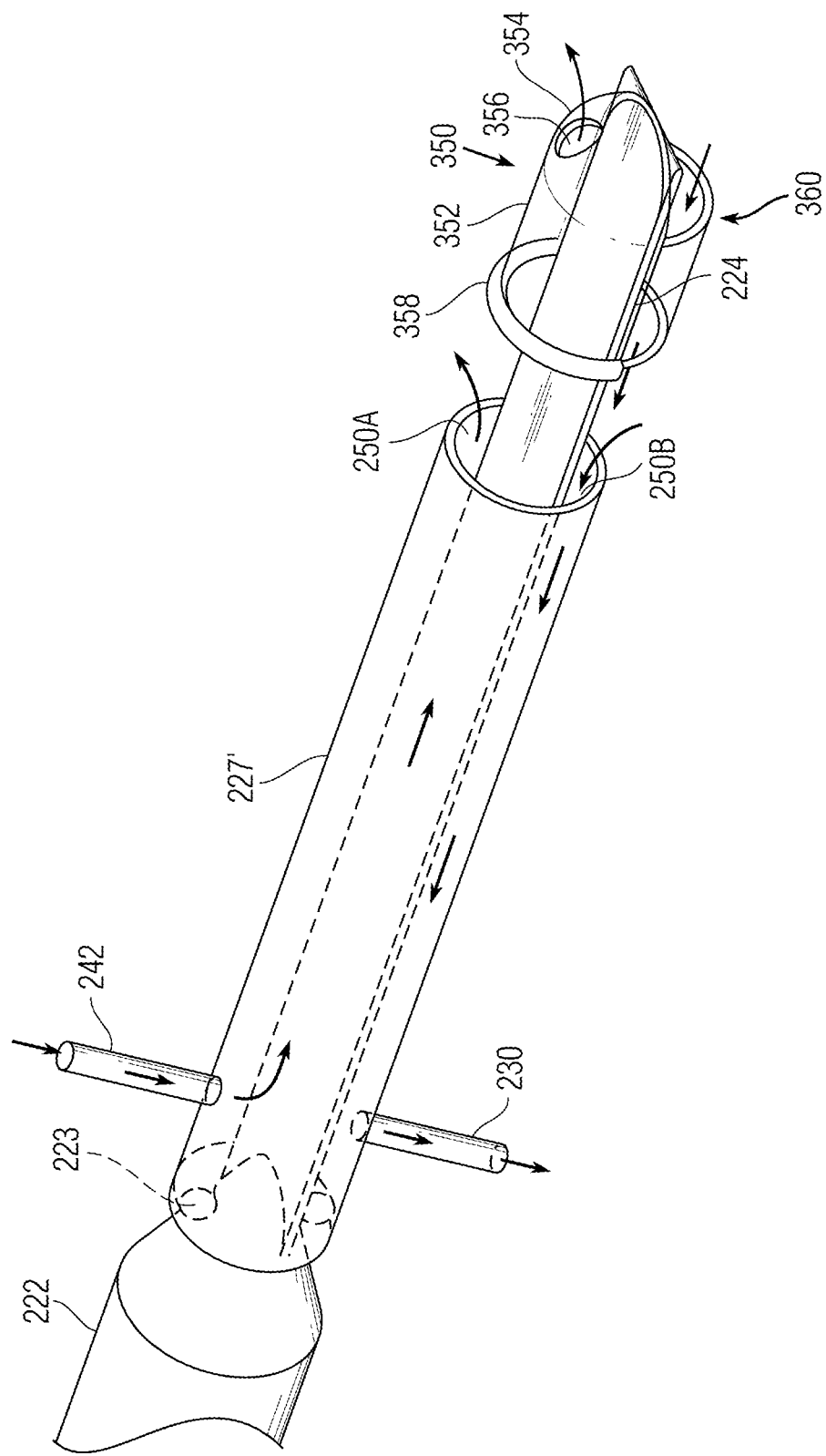
FIG. 23 shows the distal end of the work tip of FIG. 21 and the proximal end as shown in FIG. 1 so that the irrigation and aspiration connections to the work tip are illustrated.

In FIG. 23 the work tip of FIGS. 21A and B are shown connected to the hub 222 as illustrated in FIG. 1. Irrigation fluid enters the work tip at the hub through tube 242, travels within sleeve 227' above the blade 224 in channel 250A and exits near the distal end of the work tip. Similarly, fluid and tissue are aspirated at the distal end of the work tip and enter channel 250B that is within sleeve 227' below the blade 224. This aspiration material is withdrawn through tube 230 at the proximal end of the work tip. An O-ring 223 keeps the fluids from exiting the work tip over the hub 222. Thus, with the design illustrated in FIG. 23, tube connections 242, 230, respectively, are required on the handpiece to connect the irrigation channel and aspiration channel to tubes that lead to the pump and irrigation source (not shown).

Figure 24:
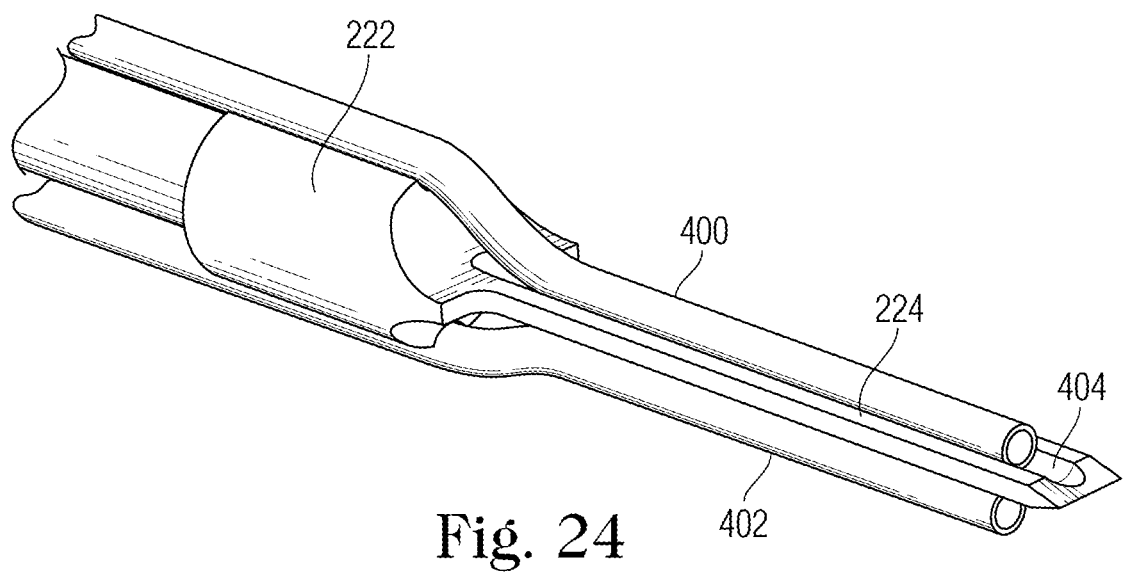
FIG. 24 shows an arrangement according to another embodiment of the invention in which flexible irrigation and aspiration tubes are provided along the blade in place of a sleeve.

The work tips shown in FIGS. 11 and 12 have a double-walled sleeve 227 that creates an irrigation channel 250', while aspiration is in channel 250 both above and below the blade 224. This design also requires tubes 242, 230 attached to the hand piece. In order to avoid the need for these connections, instead of sleeve 227' defining the path for the irrigation and aspiration fluids to and from the distal end of the work piece, tubes 400, 402 are provided as shown in FIG. 24. These tubes 400, 402 connect directly to the irrigation and aspiration pumps and extend over part of the hub 222 and along the top and bottom of the blade 224 to the distal end of the work piece. Thus, these tubes 400, 402 can be fastened to the blade and will extend into the eye of the patient during phacoemulsification. The attachment to the blade can be by way of an adhesive. In such a case the tubes will vibrate with the blade. This could cause friction between the tubes and the corneal incision, which can be harmful. To overcome this harm, a cannula can be used during the operation, such as that shown in FIG. 8 of the applicants U.S. patent application Ser. No. 16/057,653 filed Aug. 7, 2018. As an alternative, if the tubes 400, 402 are made rigid, at least from their distal end to the region of the handpiece housing, they may be fastened to the non-vibrating housing as shown for tubes 242, 230 in FIG. 30. In such a case the tubes do not vibrate with the blade and no friction is applied to the corneal incision. If necessary or desired, a band (not shown) can be placed about the distal ends of the rigid tubes to further stabilize them. If the material of the tubes is a flexible plastic, it will typically be less expensive than the material of the sleeve 227' of FIG. 23. Thus, the price of the hand piece is reduced, and it is more likely to be part of a single use disposable handpiece. Alternatively, if the tubes are made of rigid plastic up to the location of the housing and thereafter made of flexible plastic, this (while somewhat more expensive than the all-flexible tube) would nonetheless still be less expensive than the sleeve 227'.

As shown in FIG. 24 a groove 404 can be provided in the top surface of the blade to accommodate the flexible tube 400. If desired, a similar groove can be provided in the bottom surface of the blade to accommodate the flexible tube 402. An O-ring (not shown for the sake of clarity) could be located about the tubes 400, 402 and blade 224 to prevent the leakage of fluid from the eye along the blade during surgery. Further, if tubes 400, 402 are flexible and attached to the blade, the adhesive may be located in the groove 404.

Figure 25A:
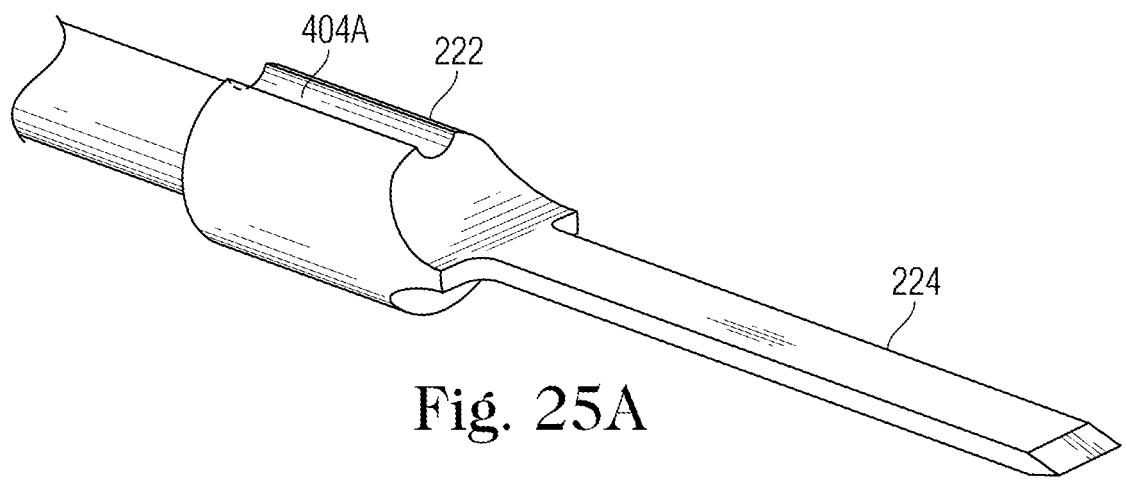
FIGS. 25A, 25B and 25C show work tips with grooves in a flat blade for flexible tubes for use with the embodiment of FIG. 24.
Figure 25B:
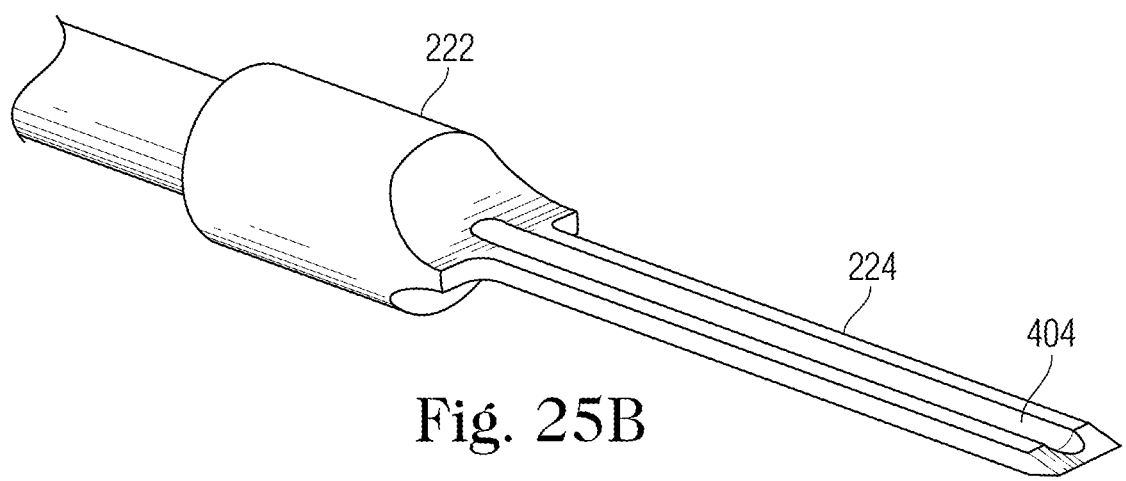
Figure 25C:
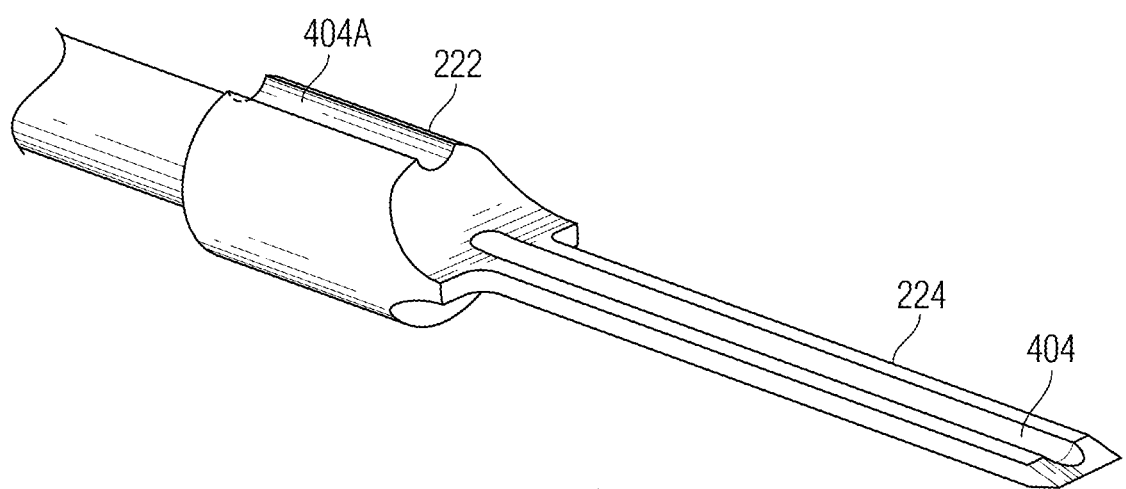

FIGS. 25A, 25B and 25C show work tips with grooves in a flat blade for flexible tubes for use with the embodiment of FIG. 24. FIG. 25A is a flat blade where a groove 404A for the flexible tube is only in the hub 222. In FIG. 25B a groove 404 in the top of the blade is show similar to that of FIG. 24. In FIG. 25C the flat blade has both groove 404 in the blade and 404A in the hub.

Figure 26A:
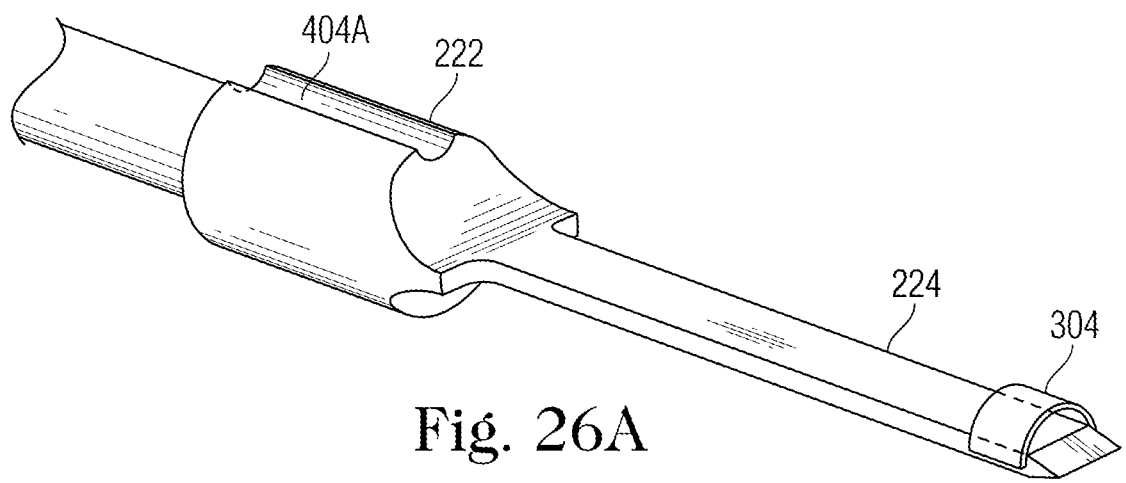
FIGS. 26A, 26B and 26C show work tips with a flat blade having a half collar at its distal end and grooves for flexible tubes for use with the embodiment of FIG. 24.
Figure 26B:
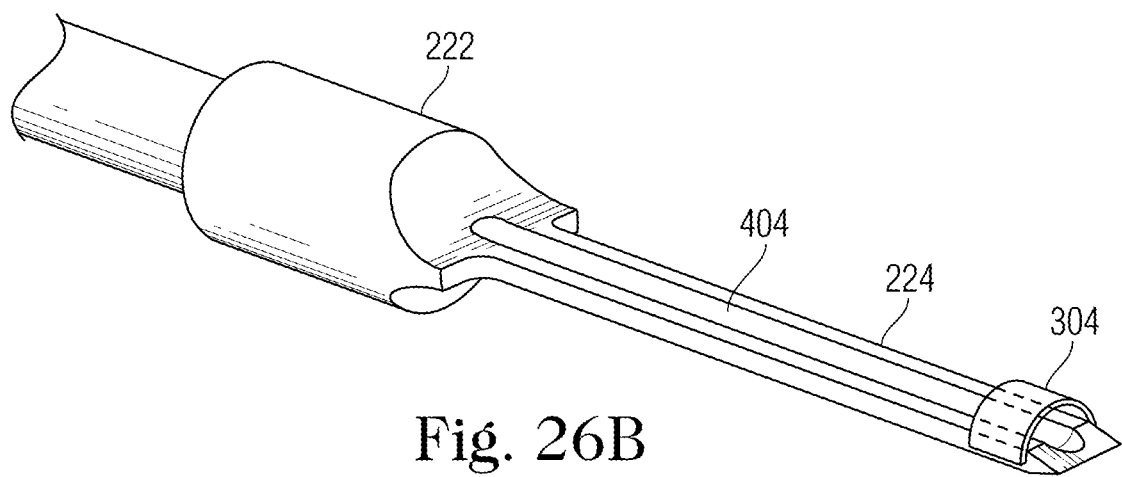
Figure 26C:
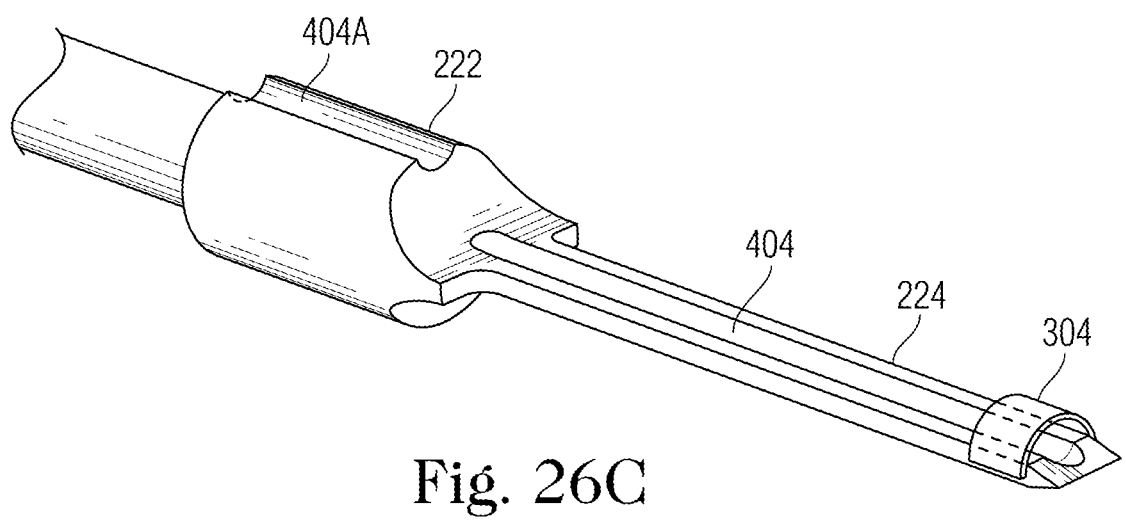

FIGS. 26A, 26B and 26C show work tips with a flat blade having a half collar at its distal end and grooves for the tubes for use with the embodiment of FIG. 24. FIG. 26A is a flat blade with a half ring or collar 304 as shown in FIGS. 9 and 10. It also has the groove 404A for the flexible tube only in the hub 222. In FIG. 26B a groove 404 in the top of the blade is show similar to that of FIG. 24. In FIG. 26C the flat blade with the half collar 304 has both groove 404 in the blade and 404A in the hub.

Figure 27A:
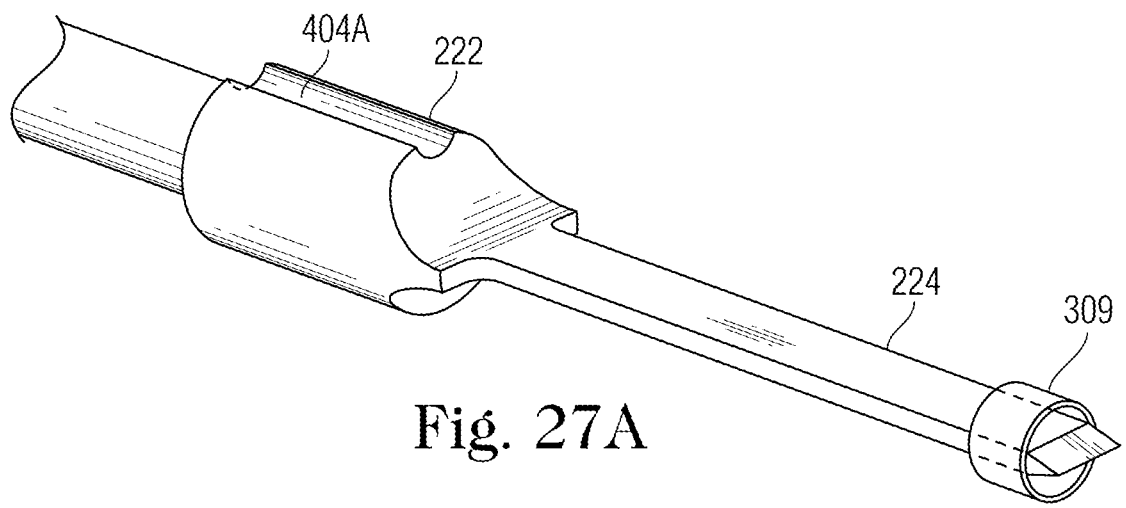
FIGS. 27A, 27B and 27C show work tips with a flat blade having a full collar at its distal end and grooves for flexible tubes for use with the embodiment of FIG. 24.
Figure 27B:
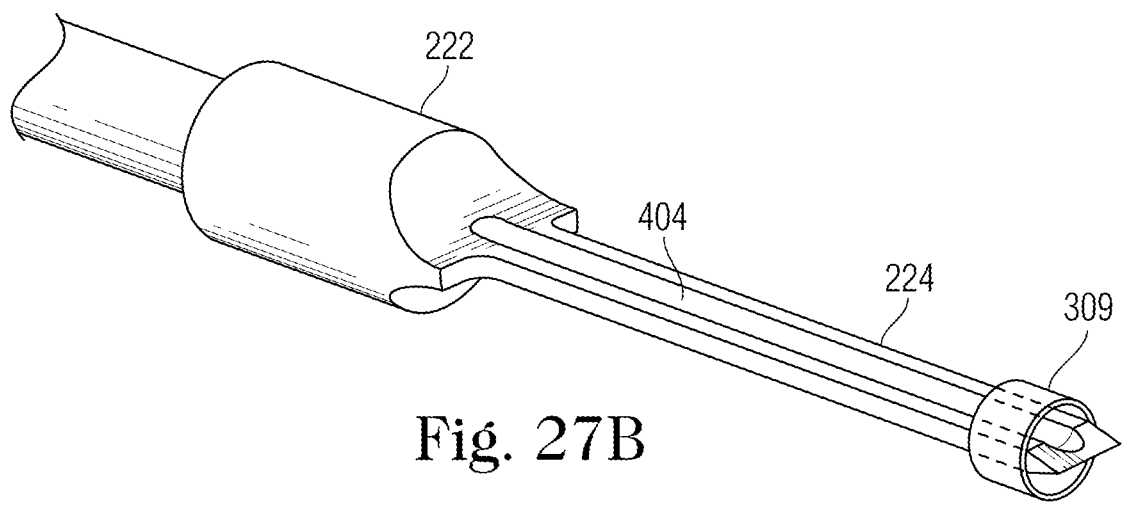
Figure 27C:
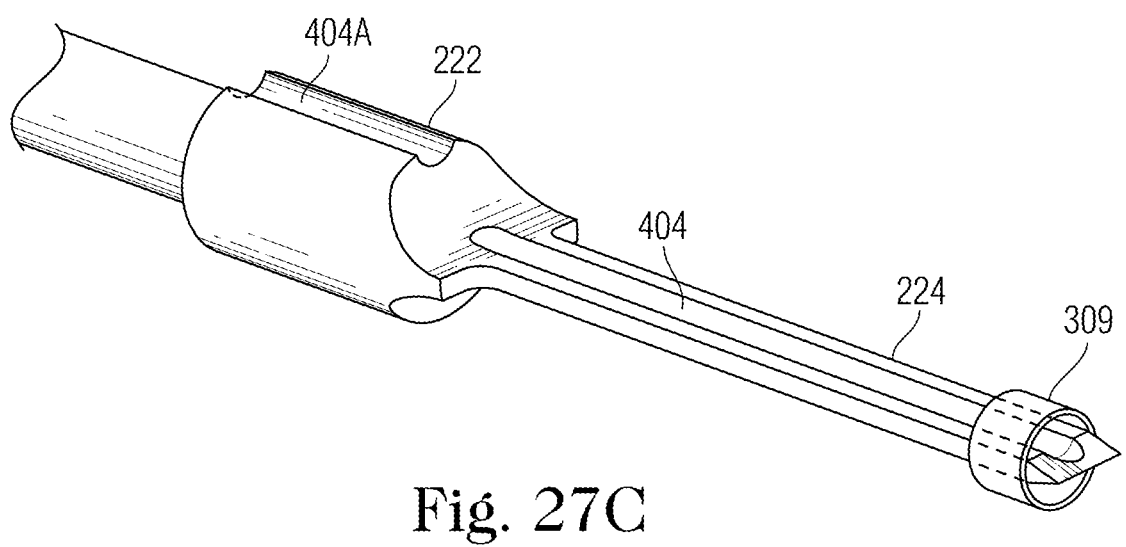

FIGS. 27A, 27B and 27C show work tips with a flat blade having a full collar or cylindrical part 309 at its distal end, and grooves for flexible tubes for use with the embodiment of FIG. 24. FIG. 27A is a flat blade with a full collar 309 similar to that in FIG. 12 where a groove 404A for the flexible tube is only in the hub 222. FIG. 27B has the groove 404 in the top of the blade. In FIG. 27C the flat blade has both groove 404 in the blade and 404A in the hub.

Figure 28A:
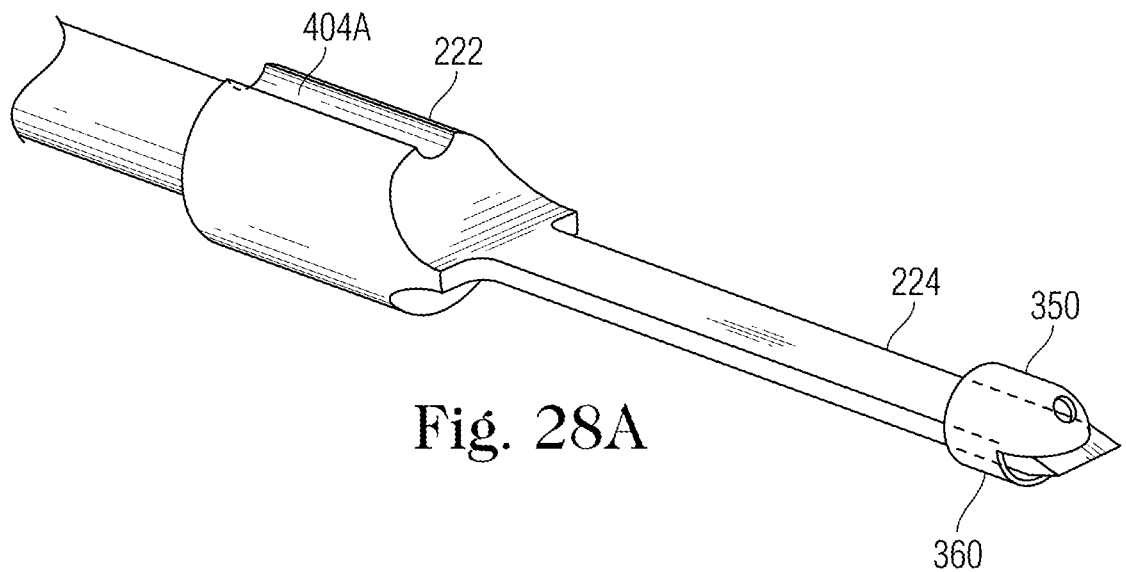
FIGS. 28A, 28B and 28C show work tips with a flat blade having a half cylindrical/hemispherical structure on top of a blade and a collar below the blade, and grooves for flexible tubes for use with the embodiment of FIG. 24.
Figure 28B:
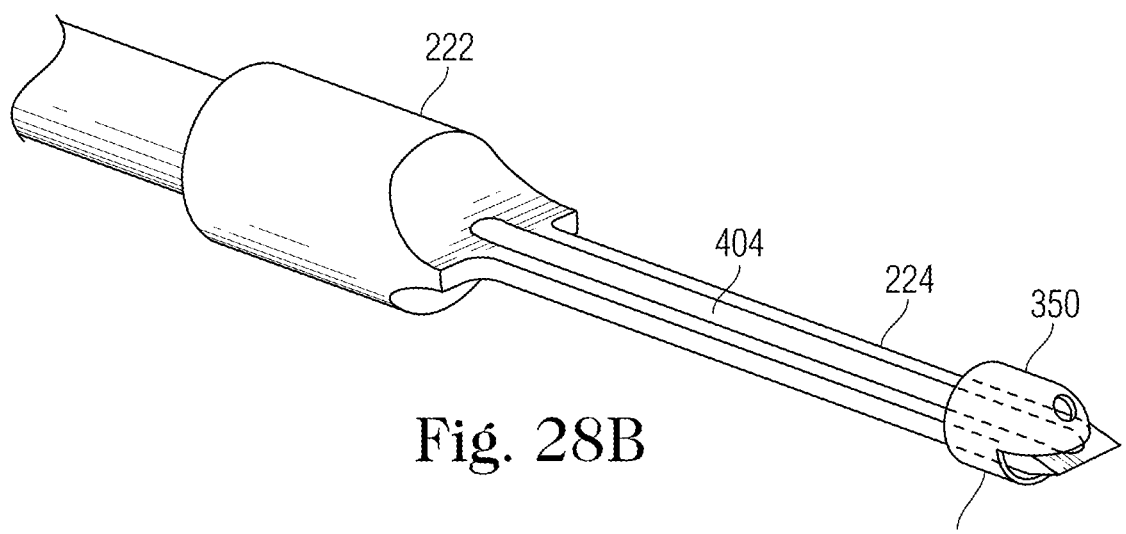
Figure 28C:
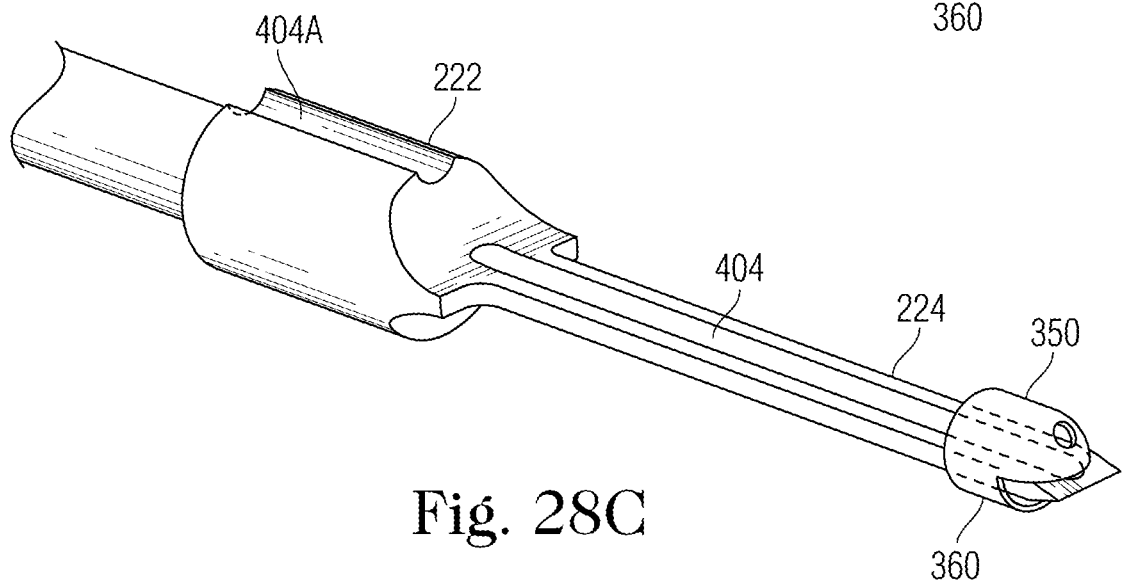

FIGS. 28A, 28B and 28C show work tips with a flat blade having a half cylindrical/hemispherical structure 350 on the upper surface of the blade and a half collar 360 on the lower surface of the blade at about the location of the half cylindrical/hemispherical structure 350 as in FIGS. 21A and 21B. FIG. 28A has the groove 404A for the tube only in the hub 222. FIG. 28B has the groove 404 in the top of the blade, and FIG. 28C has both groove 404 in the blade and 404A in the hub.

Figure 29:
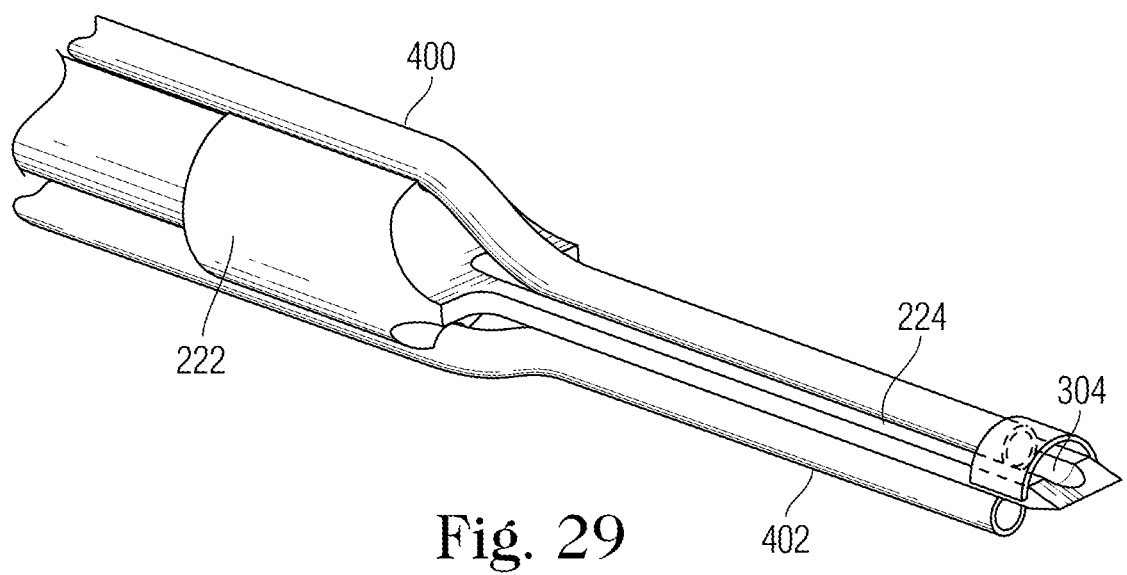
FIG. 29 shows the arrangement of FIG. 24, but with the blade of FIG. 26C.

FIG. 29 shows the arrangement of FIG. 24, but with the blade of FIG. 26C. The other blades of FIG. 26 as well as the blades of FIGS. 27 and 28 can also be substituted into this arrangement.

Figure 30:
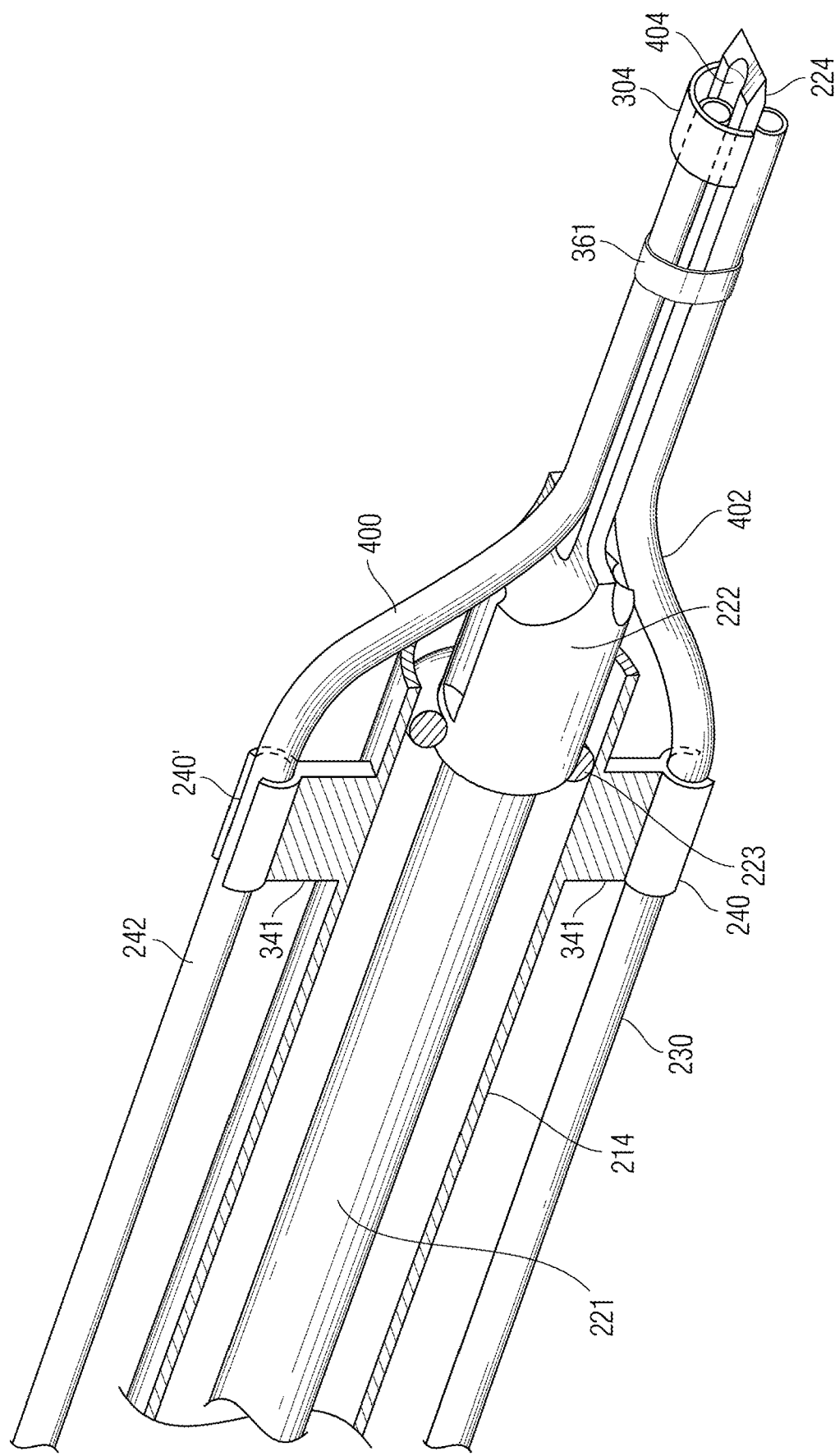
FIG. 30 shows a hand piece structure for supporting the flexible tubes with a blade according to FIG. 26C.

FIG. 30 shows a hand piece structure for supporting the tubes 242, 400 and 230, 402 with a blade according to FIG. 26C with a half collar 304. The tubes are supported in holders 240, 240' that are attached to the hand piece housing 214 by flanges 341. O-ring 223 riding on hub 222 keeps fluid from entering the hand piece housing and engaging the connecting body and the piezoelectric transducers (221). In this case the parts of the tubes 400, 402 may be rigid and the parts of the tubes 242, 230 may be flexible. The rigid part is supported at its proximal end by flanges 341 and may, if desired, be supported at its distal end by a band 361.

Figure 31:
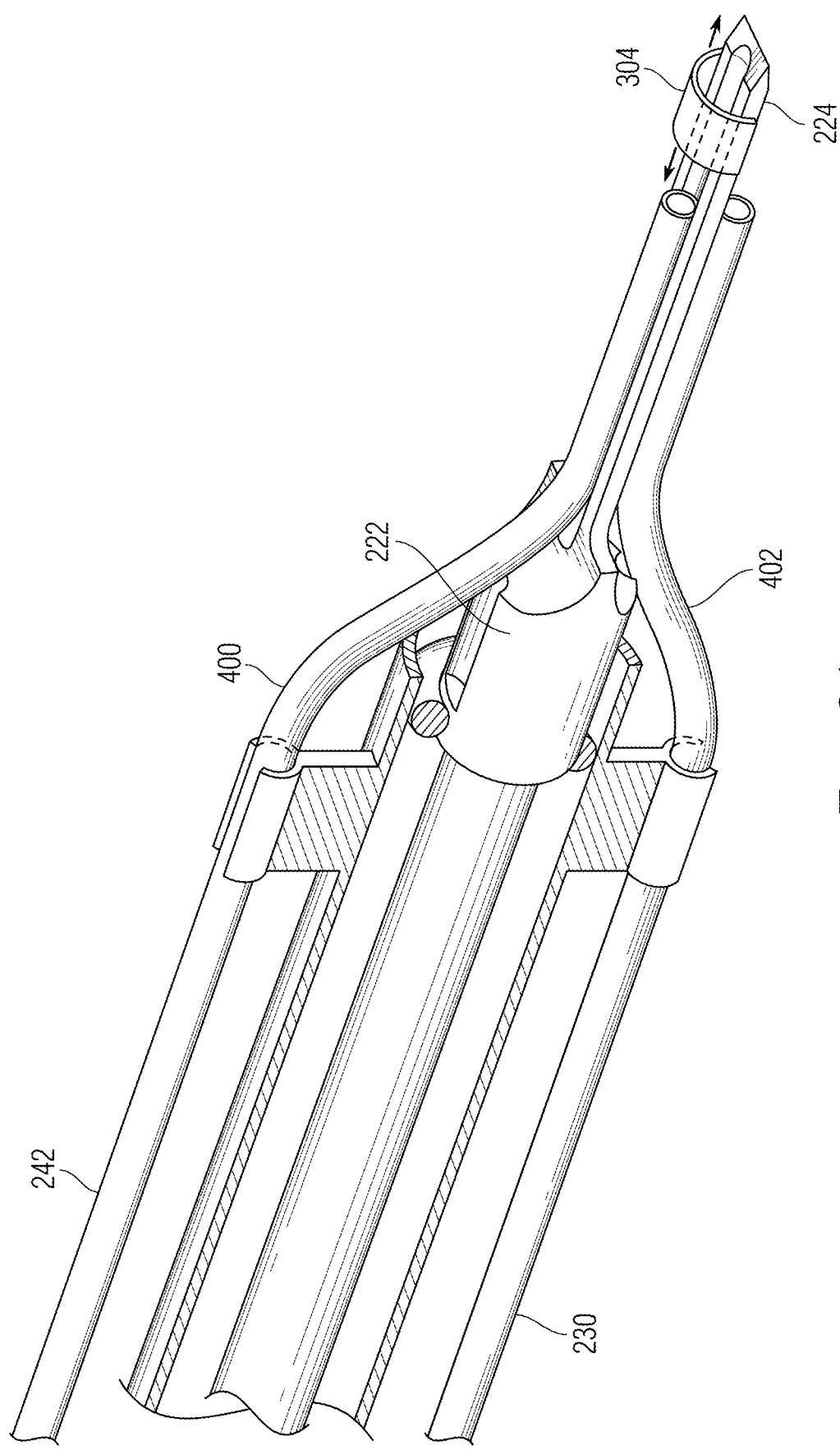
FIG. 31 shows a similar structure in which the flexible tubes terminate short of the distal end of the blade.

FIG. 31 shows a structure similar to FIG. 30, but in which the flexible tubes 400, 402 terminate short of the distal end of the blade 224 and the half collar 304. As will be further explained, if the distal and proximal edges of the half collar 304 are made sharp enough to cut cataract tissue, improved phacoemulsification occurs. The edges of the collar participate in the cutting of the tissue along with the blade 224. Further, because of the proximal edge of the collar, pieces of tissue above the blade that approach the aspiration tube 402 are cut, so that occlusion of the tube does not occur. This effect is even greater if a full cylindrical collar 309 as shown in FIG. 27 is used because the lower proximal edge is just in front of the aspiration tube opening.

Figure 32A:
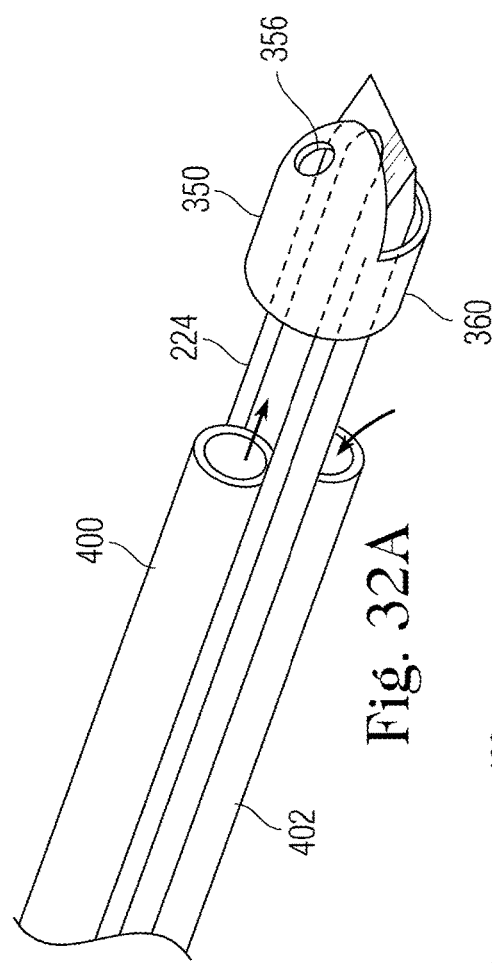
FIG. 32A shows the tip in the orientation of FIG. 28
Figure 32B:
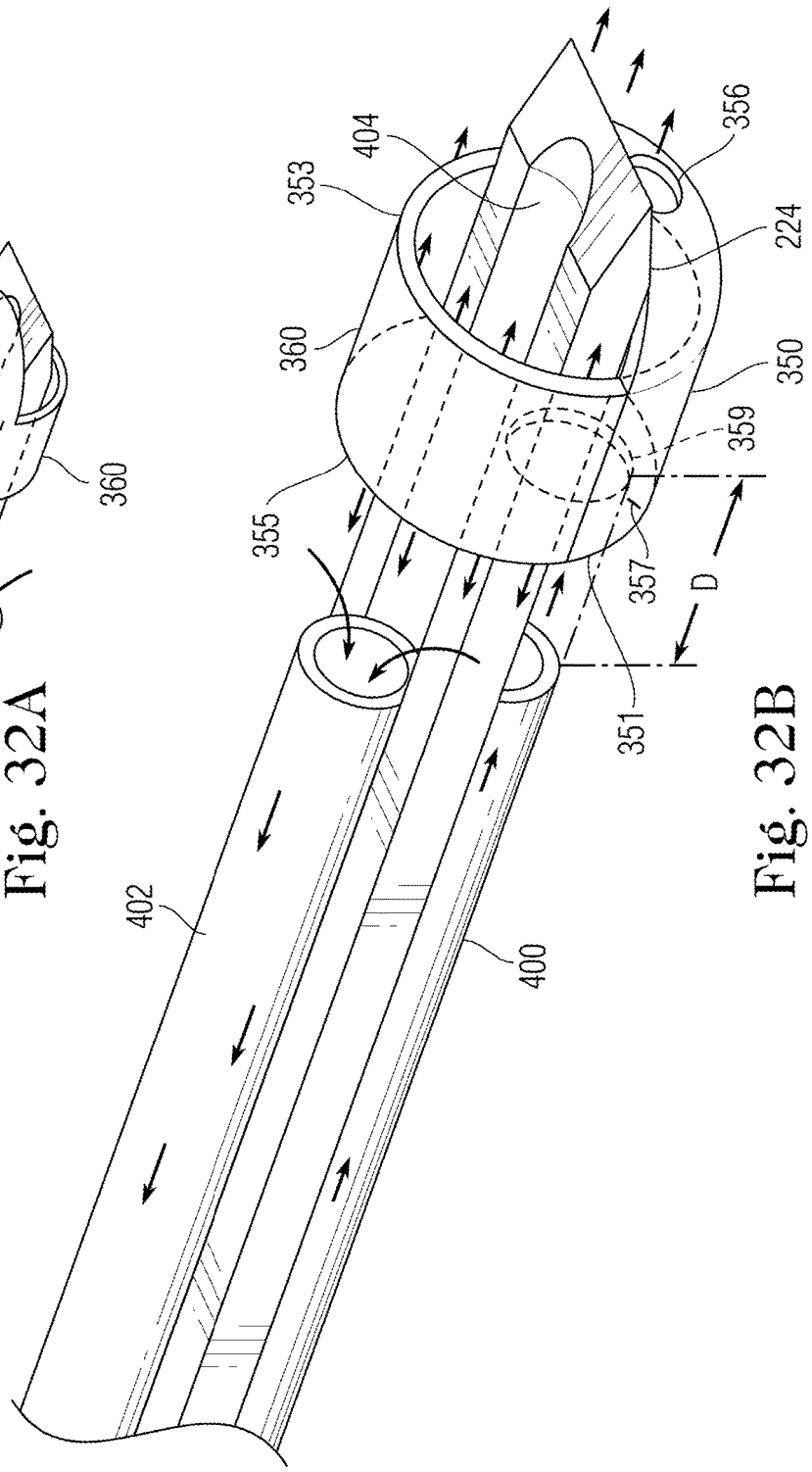
FIG. 32B shows the tip invented to illustrate the forces that promote phacoemulsification and prevent occlusion of the aspiration tube.

FIG. 32A is an enlarged version of work tip 350 of FIG. 28. In FIG. 32B the tip is shown inverted so that aspiration tube 402 is shown in the upper part of the drawing for a better view and the irrigation tube 400 is shown on the opposite side of the blade. The work tip has the cylindrical/hemispherical portion 350 on the blade toward the bottom of the drawing and the half cylindrical or collar portion 360 on the blade toward the top of the drawing.

The biggest problem in cataract surgery is that with the current technology, in which a hollow needle is used in place of the blades shown herein, the needle can become occluded with a piece of cataract tissue during aspiration, causing suction to build up in the line. When the occlusion is released, the tissue is grabbed by the sudden higher suction pressure in the needle, which damages the delicate intraocular structures, especially the posterior capsule. When the posterior capsule is broken, vitreous will enter the anterior chamber. As a result, anterior vitrectomy has to be performed to clean up the vitreous.

As shown in FIG. 32B the aspiration tube 402 is separated from the working tip by a longitudinal distance D. During a phacoemulsification procedure the end is vibrated at an ultrasonic frequency. During the forward stroke both the sharp blade tip and the distal end of the collar 353 impact the cataract tissue. During the reverse stroke, the proximal end of the collar 355 impacts any tissue broken off during the forward stroke before it can reach the opening of the aspiration tube 402. Thus, there are no large particles in the vicinity of the aspiration tube 402 opening. As a result, it is not possible to occlude the aspiration tube. All the material in front of the aspiration tube will be emulsified by the ultrasonic energy from the front of the collar, back of the collar, and the front of the blade.

The distance between the aspiration tube and the collar can be predetermined and fixed. As an alternative, the distance can be made adjustable by the surgeon. In effect the surgeon pulls on the tube in the proximal direction when it is not fixed to the blade by an adhesive. For example, the arrangement of FIG. 34C can be used for this purpose.

With a needle working tip, it is the end of the tip that vibrates with a substantial stroke, forcing the layers of material in front of it (fluid and/or cataract tissue) not only to oscillate but to move and give way, creating a shock wave. With the present invention, because the blade and front edge of the half collar are larger than a needle tip, the shock wave is even greater. When the tip advances, it not only generates an acoustical traveling wave and possibly feeds a standing wave; it also moves a large mass of fluid in front of it, creating high velocity streams that can exceed 20 m/sec (72 km/Hr) within some time period. When the tip is retracted, those layers of material impacted cannot follow, and so the fluid continues to move forward due to inertia and a lack of sheer strength. As a result, a void is formed, which then collapses in a disorderly manner. The resulting implosion or "cavitation" sends shock waves again throughout the fluid contents. The void is filled from the side of the tip with new fluid causing circulation and streaming in front of the tip. The process repeats on the next stroke.

Even within a hollow needle work tip, a form of material motion is present on the interior surface of the vibrating structure. On the surface of the hole in the tip of the needle and connecting body an elliptical motion of particles is established from the tip into the aspiration line. The surface wave causes the particles to move along a clockwise elliptical trajectory in the direction of propagation. Consequently, when the tip is vibrating, the surface wave is imposing motion to the aspirated fluid in the direction of motion of the tip. The size of the ellipse, the inclination of its axis, and the direction of the path on the trajectory during the back and forth motion of the tip determines a resultant vector that aids the evacuation process. At maximum stroke, the regular tip and the connecting body of the emulsifier produce a differential pressure of up to 400 mm $H_2O$ or 30 mm Hg of suction with a needle. This force is believed to be higher with the structure of FIG. 32.

During the forward stroke of the work tip the distal edge 353 of the half collar or half cylinder in FIG. 32 engages in the main emulsification of the cataract tissue along with the sharp edge of blade 224. The proximal edge 355 also engages in emulsification during the back stroke in the area just in front of the aspiration tube 402 and prevents occlusion of that tube. Once phacoemulsification is complete, irrigation/aspiration (I/A) cleanup is required. Typically, this is done without vibration and at a lower suction force. In order to implement this, the blade and tip 350, 360 are withdrawn into alignment with the tubes 400, 402. Aspiration and irrigation are reversed so that aspiration occurs in tube 400. However, when withdrawn, a wall 357 at the proximal end of the cylindrical/hemispherical portion 350 engages the end of tube 400 at the location of an opening 359 in the wall. As a result, the aspiration force in tube 400 is primarily applied to the interior of the portion 350. In turn this causes the aspiration cleanup force to be applied to the small hole 356. This, along with the smooth surface of the portion 350, creates an ideal tool for cleanup.

Figure 33A:
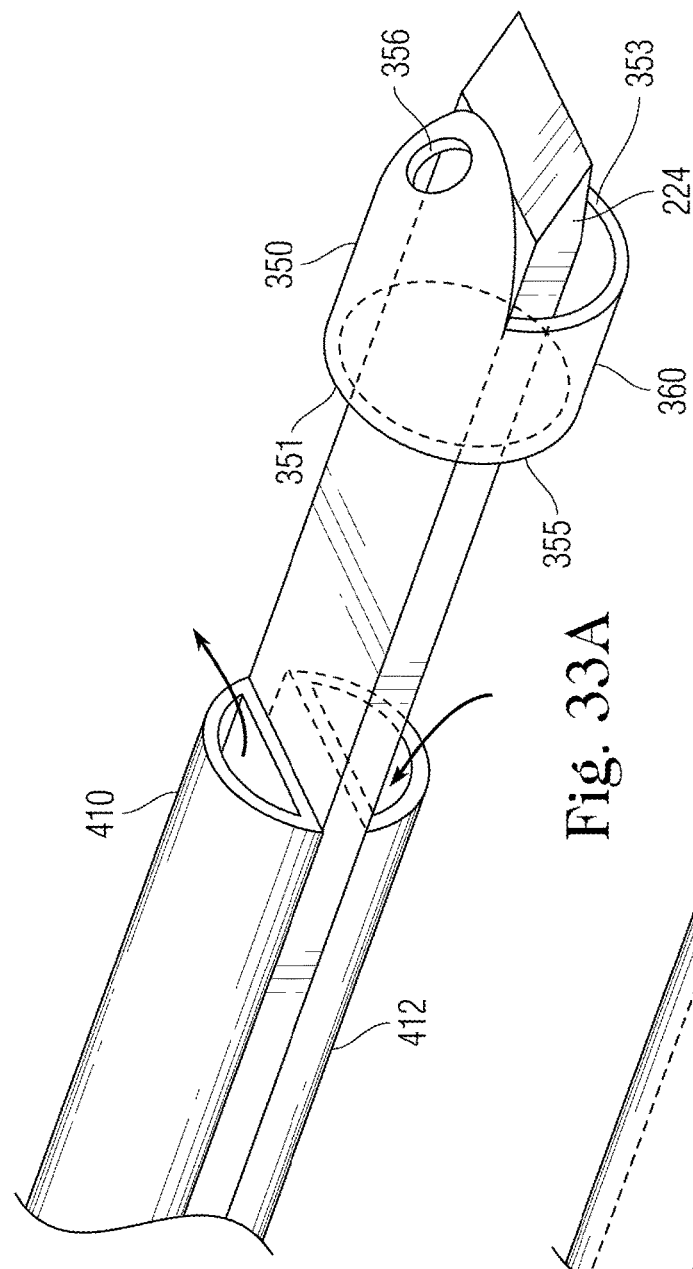
FIG. 33A illustrates illustrate the work tip of FIG. 32 in the orientation of FIG. 33A with D-shaped irrigation and aspiration tubes that are at a distance from the tip.
Figure 33B:
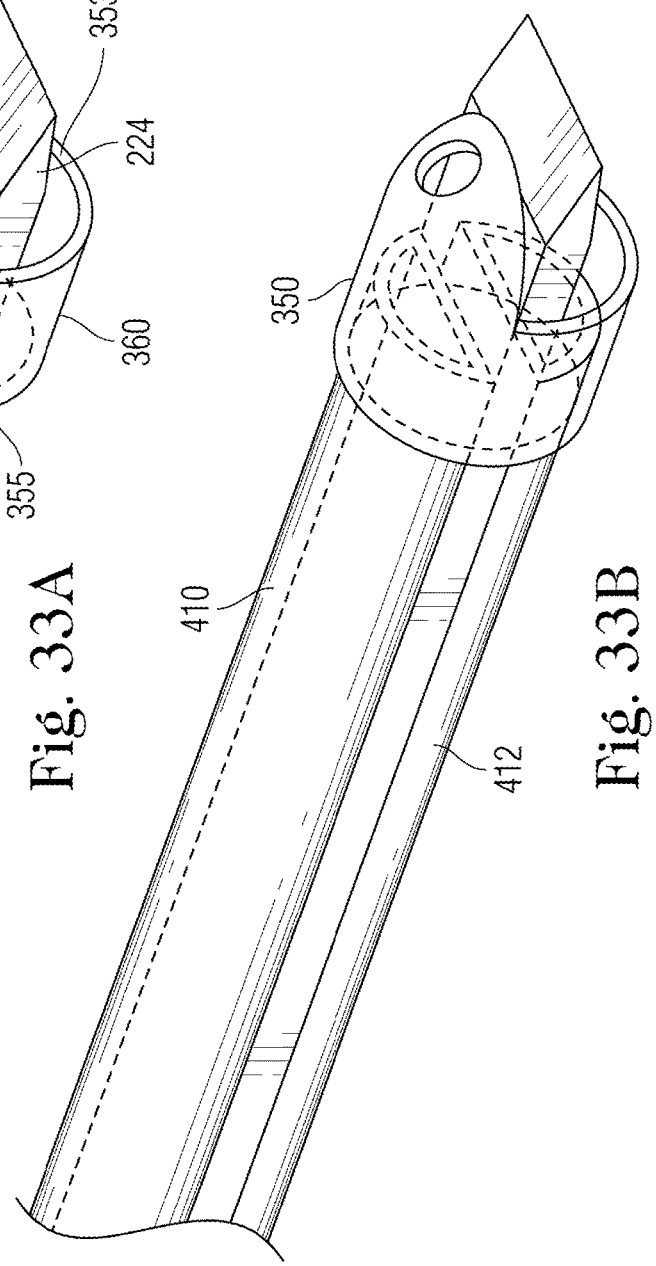
FIG. 33B shows the arrangement of FIG. 33A wherein the tip has been slid back so that the tubes enter and seal it.

FIG. 33 illustrates the blade with the structure shown in FIG. 32A but with D-shaped tubes 410, 412. In the extended position shown in FIG. 33A, the vibration of the portion 360 allows its edges 353, 355 to emulsify the cataract tissue along with the blade 224. Edge 355 is particularly effective in eliminating occlusion of the aspiration line 412. Proximal edge 351 of the portion 350 may also engage in emulsification to eliminate occlusion.

In this arrangement the portion 350 does not require a back wall 357 and a hole 359. Instead, when the tip is withdrawn into engagement with the tubes, 410 slides into the internal diameter of 350 and 412 slides into the internal diameter of 360. As regards the cylindrical/hemispherical portion 350, the tube 410 blocks most of the proximal end of that portion. Thus, during cleanup, when tube 410 is switched to aspiration, the small bits of tissue will be drawn through hole 356.

Figure 34A:
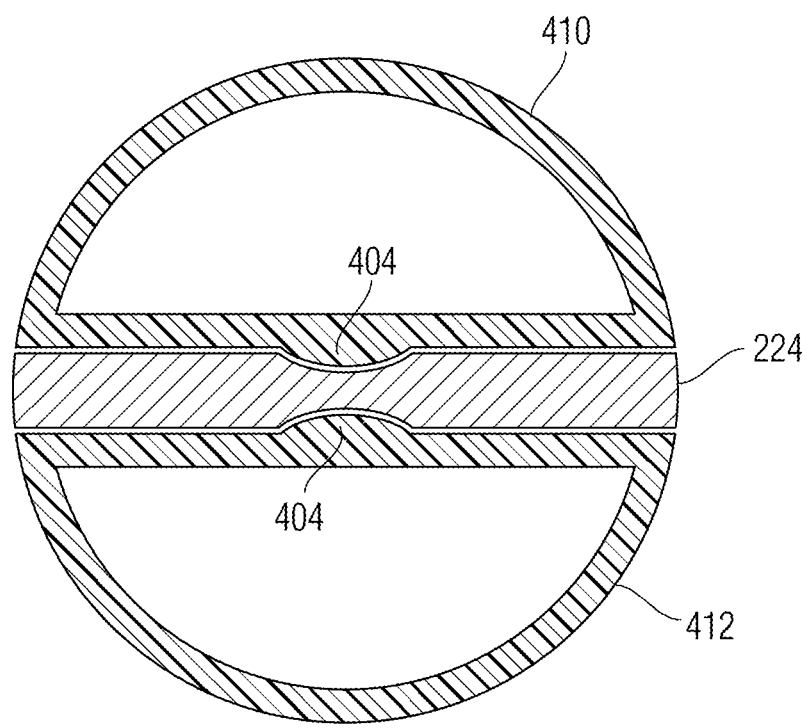
FIG. 34A shows a cross section of the D-shaped tubes fastened to the top and bottom of a blade by adhesive.
Figure 34B:
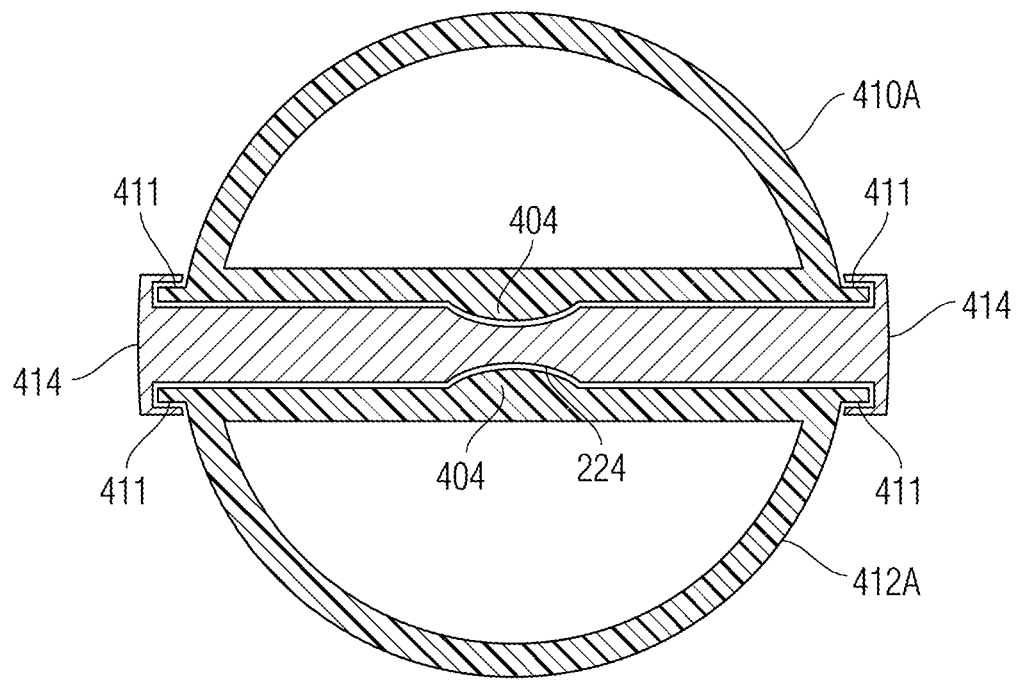
FIG. 34B shows the D-shaped tubes inserted into grooves formed at the edges of the blade and FIG. 34C shows protrusions from D-shaped tubes captured in recesses of the blade.
Figure 34C:
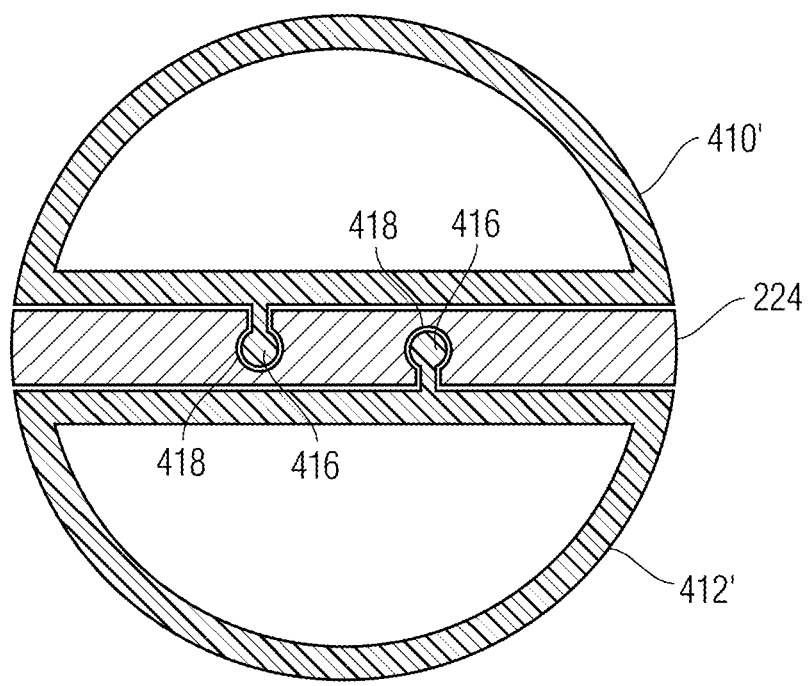

As mentioned above, when flexible tubes are used, they can be attached to the blade. FIG. 34 shows the D-shaped tubes 410, 412 fastened to opposite sides of blade 224. Using the D-shapes gives the overall structure a round shape for ease of insertion in a corneal incision. FIG. 34A shows D-shaped tubes 410, 412 fastened to the top and bottom of a blade 224 by adhesive. A portion of the tube surface protrudes into the grooves 404. The blade can also be manufactured without these grooves. FIG. 34B shows D-shaped tubes mechanically trapped on the blade. In this embodiment the D-shaped tubes have flanges 411 that are captured by grooves at the edges 414 of the blade. FIG. 34C shows protrusions 416 from each D-shaped tube that are captured in recesses 418 on the top and bottom of the blade 224. The grooves 418 have entrances at the proximal end of the blade that allow the tubes to be slid into the grooves. This last embodiment provides a smooth outer circumference to the structure and secure mechanical interlocking between the tubes and blade.

In phacoemulsification surgery, it is common to use a second instrument in the form of a very small rod to manipulate pieces of cataract toward the ultrasonic tip or to irrigate the site. FIG. 35A illustrates a phacoemulsification procedure using a second instrument. However, the arrangement in FIG. 35A is different in that the second instrument has an aspiration port. Prior to the present invention, cataract surgery has involved removal of cataract tissue using only a single vibrating hollow titanium aspiration tube.

With the collar (or hybrid) working tip of the present invention, the aspiration can be separated from the emulsification tool and located in a second tool. Furthermore, the second tool or instrument can be optionally aspiration only, irrigation only, or a combination of both.

The procedure shown in FIG. 35A makes use of a handpiece 502, which may be of the form shown in FIG. 31 but may also be any of the other types of handpieces with blades shown throughout the present application. Further, the handpiece 502 can be used as-is as shown in FIG. 31 (with aspiration and irrigation tubes above and below the blade) with a second aspiration tube 504, or the aspiration tube can be removed from the handpiece. In the latter case, the handpiece would have only the irrigation tube 400 (242) and the second tube 504 would be used for aspiration. All the various configurations of different ultrasonic tips that have the 2-tube arrangement above and below the blade may benefit from a second instrument that aspirates.

During a phacoemulsification procedure the vibrating handpiece 502 is brought into engagement with the cataract 510 so that pieces of the cataract are broken up and emulsified. The second instrument 504 may be used to irrigate the operating site, or it can be used to aspirate some of the emulsified tissue, or it may be used for both irrigation and aspiration.

FIG. 35B shows the lumen of the second instrument when used for aspiration or irrigation. FIG. 35C shows the lumen for the second instrument when used for both aspiration and irrigation, respectively, on either the top or bottom channels.

Surgical procedures have been carried out to test the effectiveness of the inventions disclosed herein. In one such procedure the handpiece of FIG. 1 was used to conduct phacoemulsification surgery on an animal eye. This handpiece had a blade as the cutting instrument with separate irrigation and aspiration tubes. The results showed enhanced phacoemulsification due to the blade. Also, because the tubes were outside the handpiece, a less expensive design was presented. This design was made even less expensive by making the blade one-piece with the connecting body as disclosed in U.S. patent application Ser. No. 15/821,137 filed Nov. 22, 2017, which is incorporated herein by reference in its entirety.

Another surgical procedure was carried out to test the effectiveness of the handpiece of FIG. 32, but with an anterior chamber maintainer (ACM) instead of an irrigation tube along the blade. This handpiece was a hybrid, i.e., the same handpiece could perform phacoemulsification and subsequent irrigation/aspiration cleanup. It had a reduced cost and could be made disposable. Further, the procedure demonstrated that the handpiece had the additional benefit of preventing occlusion of the aspiration tube, which in turn had the effect of eliminating post-occlusion surges of aspiration material due to the buildup of vacuum in the aspiration tube when it is blocked. Thus, one of the major complications of cataract surgery—the breaking of the posterior capsule—is eliminated.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A one-piece work tip for a surgical hand piece comprising:
    a solid flat blade with a sharp distal end having its proximal end connectable to a source of ultrasonic energy in the hand piece, said blade having first and second flat opposite exterior surfaces along its length;
    a solid hub formed as an expanded cylindrical portion of the proximal end of the blade and providing a connection to the source of ultrasonic energy;
    an open groove located in and along the entire length of the hub and being aligned with the first flat exterior surface of the blade; and
    wherein said aligned open groove is adapted to receive one of an irrigation or aspiration tube extending on and along the first flat exterior surface of the blade and extending so as to be at least partially embedded within the entire length of the aligned open groove of the hub.

2. The one-piece work tip according to claim 1 further including a portion of the aligned open groove located along the first flat exterior surface of the blade, wherein said portion of the aligned open groove on the first flat exterior surface of the blade is adapted to receive one of the irrigation or aspiration tubes so as to be embedded in the portion of the aligned open groove in the first flat exterior surface of the blade.

3. The one-piece work tip according to claim 2 wherein the second flat exterior surface is configured to receive the other of the irrigation or aspiration tube, said second flat exterior surface of the blade also having a groove adapted to receive the other of the irrigation or aspiration tube extending along the second flat exterior surface of the blade so as to be embedded in the groove of the second flat exterior surface of the blade.

\* \* \* \* \*